US011045258B2

(12) United States Patent
Inouye et al.

(10) Patent No.: US 11,045,258 B2
(45) Date of Patent: Jun. 29, 2021

(54) GUIDE APPARATUS FOR DELIVERY OF AN ELONGATE DEVICE AND METHODS OF USE

(71) Applicant: INTUITIVE SURGICAL OPERATIONS, INC., Sunnyvale, CA (US)

(72) Inventors: Matthew D. Inouye, Foster City, CA (US); David W. Bailey, Portola Valley, CA (US); Stephen J. Blumenkranz, Los Altos, CA (US); Matthew D. Rohr Daniel, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 234 days.

(21) Appl. No.: 16/315,922

(22) PCT Filed: Jul. 7, 2017

(86) PCT No.: PCT/US2017/041160
§ 371 (c)(1),
(2) Date: Jan. 7, 2019

(87) PCT Pub. No.: WO2018/009841
PCT Pub. Date: Jan. 11, 2018

(65) Prior Publication Data
US 2019/0247128 A1 Aug. 15, 2019

Related U.S. Application Data

(60) Provisional application No. 62/359,957, filed on Jul. 8, 2016.

(51) Int. Cl.
*A61M 25/01* (2006.01)
*A61B 34/20* (2016.01)
(Continued)

(52) U.S. Cl.
CPC .............. *A61B 34/20* (2016.02); *A61B 34/30* (2016.02); *A61B 34/35* (2016.02); *A61B 34/71* (2016.02);
(Continued)

(58) Field of Classification Search
CPC ... A61B 2034/301; A61B 34/30; A61B 34/20; A61B 34/37; A61B 34/35; A61B 34/71;
(Continued)

(56) References Cited

U.S. PATENT DOCUMENTS 5,957,892 A 9/1999 Thorne
6,331,181 B1 12/2001 Tierney et al.
(Continued)

FOREIGN PATENT DOCUMENTS

CN 103221727 A 7/2013
CN 103338712 A 10/2013
(Continued)

OTHER PUBLICATIONS

Extended European Search Report for Application No. EP17825007.2 dated Feb. 3, 2020, 8 pages.
(Continued)

*Primary Examiner* — Katherine M Shi
(74) *Attorney, Agent, or Firm* — Haynes and Boone, LLP

(57) ABSTRACT

An apparatus for guiding an elongated flexible instrument comprises a variable-length support assembly including a first end, a second end, a plurality of support member pairs, and a plurality of eyelets movably coupled to at least one support member pair and configured to receive the elongated flexible instrument. The variable-length support assembly is configured to selectively transition from a compressed configuration to an expanded configuration along a longitudinal central axis, and the plurality of eyelets are adapted to support the elongated flexible instrument as the elongated (Continued)

flexible instrument is advanced along the longitudinal central axis. Each of the plurality of eyelets includes a tapered alignment member configured to contact a tapered alignment member of an adjacent eyelet to move the plurality of eyelets into alignment along the longitudinal axis as the variable length assembly transitions from the expanded configuration to the compressed configuration.

20 Claims, 31 Drawing Sheets

(51) Int. Cl.
*A61B 34/00* (2016.01)
*A61B 34/35* (2016.01)
*A61B 34/30* (2016.01)
*A61B 90/00* (2016.01)

(52) U.S. Cl.
CPC ..... *A61M 25/01* (2013.01); *A61B 2034/2051* (2016.02); *A61B 2034/2059* (2016.02); *A61B 2034/2061* (2016.02); *A61B 2034/301* (2016.02); *A61B 2090/364* (2016.02); *A61B 2090/371* (2016.02)

(58) Field of Classification Search
CPC ............ A61B 1/0055; A61B 2017/003; A61B 2017/00305; A61B 2017/00991; A61M 2025/0059; A61M 25/0029; A61M 25/0053; A61M 25/0054; A61M 25/01; A61M 25/0102; Y10T 29/53261; Y10T 29/53265; F16L 3/1222
See application file for complete search history.

(56) References Cited

U.S. PATENT DOCUMENTS

| | | |
|---|---|---|
| 6,380,732 B1 | 4/2002 | Gilboa et al. |
| 6,389,187 B1 | 5/2002 | Greenaway et al. |
| 6,491,701 B2 | 12/2002 | Tierney et al. |
| 7,772,541 B2 | 8/2010 | Froggatt et al. |
| 8,900,131 B2 | 12/2014 | Chopra et al. |
| 8,961,533 B2 | 2/2015 | Stahler et al. |
| 9,259,274 B2 | 2/2016 | Prisco et al. |
| 9,452,276 B2 | 9/2016 | Duindam et al. |
| 2004/0254566 A1 | 12/2004 | Plicchi et al. |
| 2006/0013523 A1 | 1/2006 | Childers et al. |
| 2012/0071895 A1* | 3/2012 | Stabler .................... A61B 6/12 606/130 |
| 2014/0343568 A1 | 11/2014 | Fenech et al. |
| 2015/0327939 A1 | 11/2015 | Kokish et al. |

FOREIGN PATENT DOCUMENTS

| | | |
|---|---|---|
| EP | 2626033 A2 | 8/2013 |
| WO | WO-2011100110 A1 | 8/2011 |
| WO | WO-2016018618 A1 | 2/2016 |

OTHER PUBLICATIONS

International Preliminary Report on Patentability for Application No. PCT/US2017/041160, dated Jan. 17, 2019, 11 pages.
International Search Report and Written Opinion for Application No. PCT/US2017/041160, dated Oct. 6, 2017, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

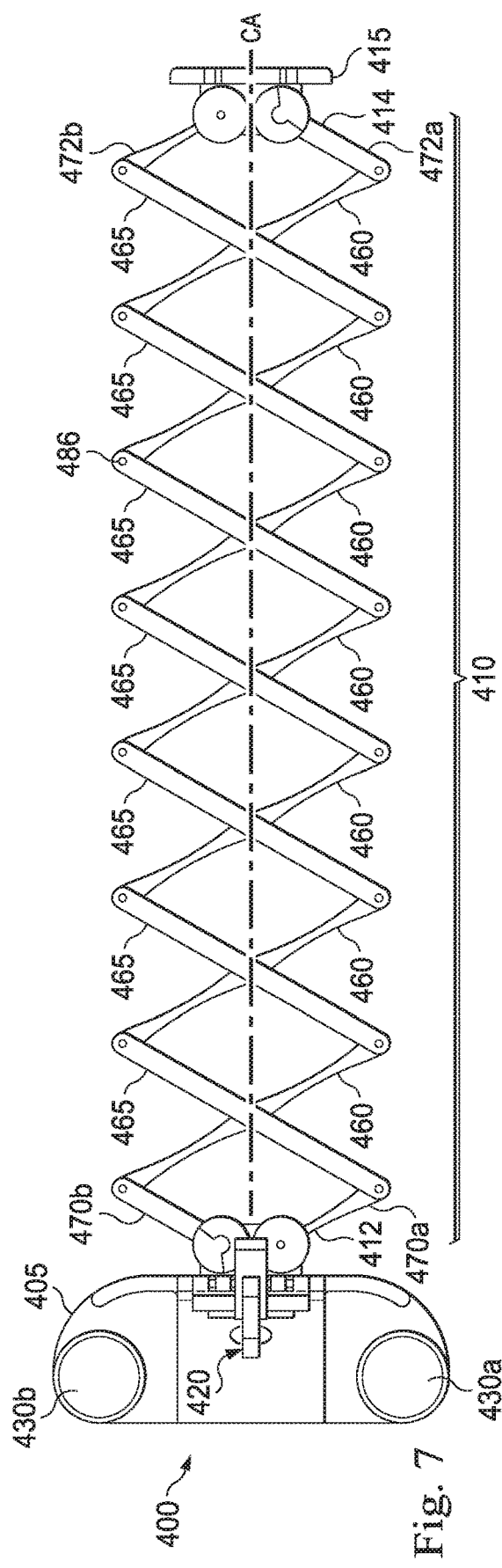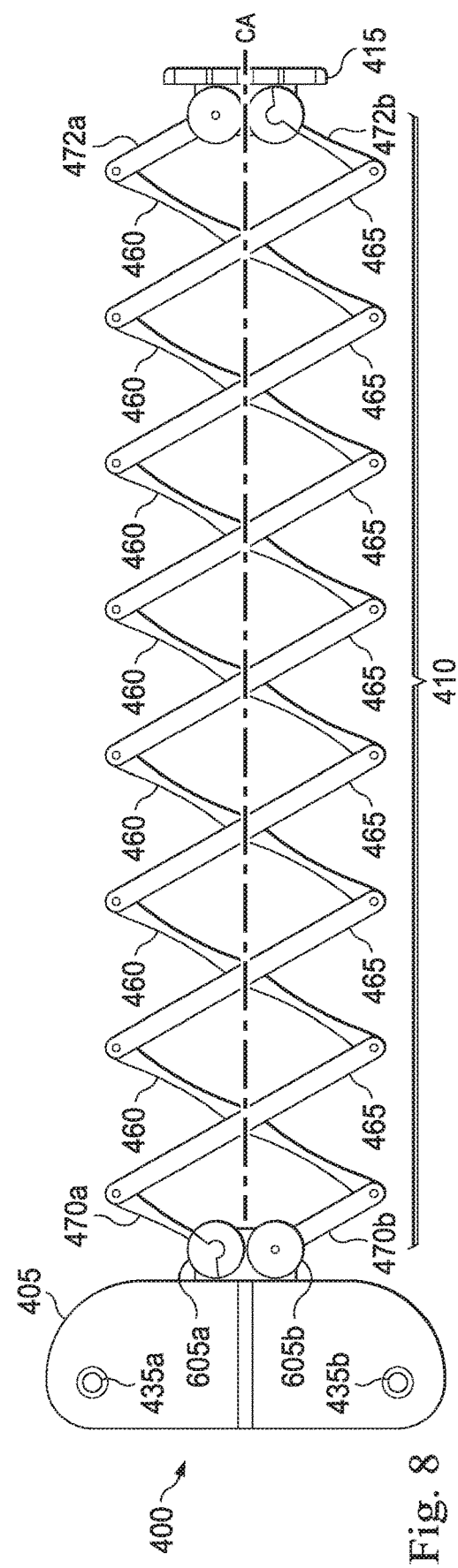

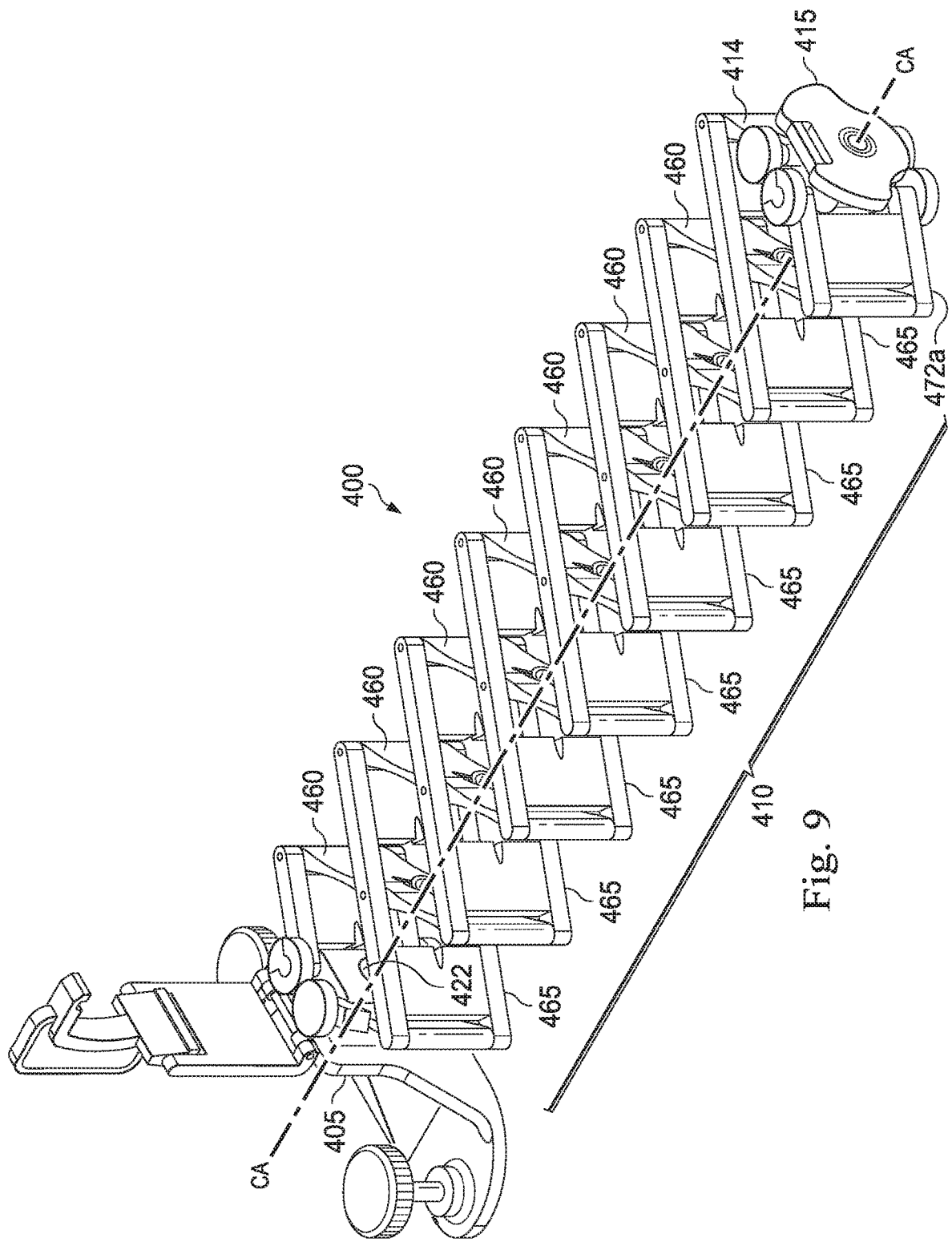

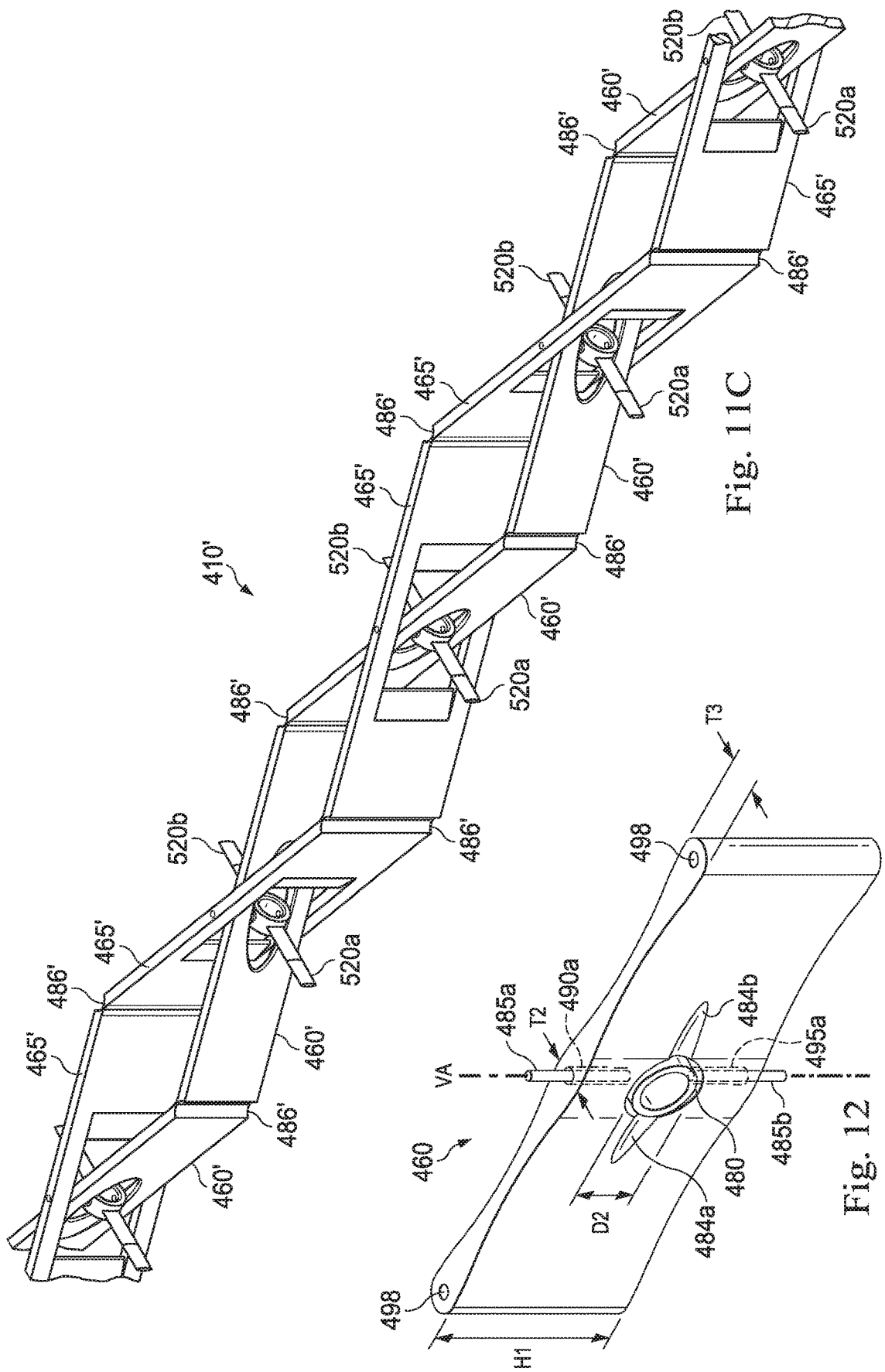

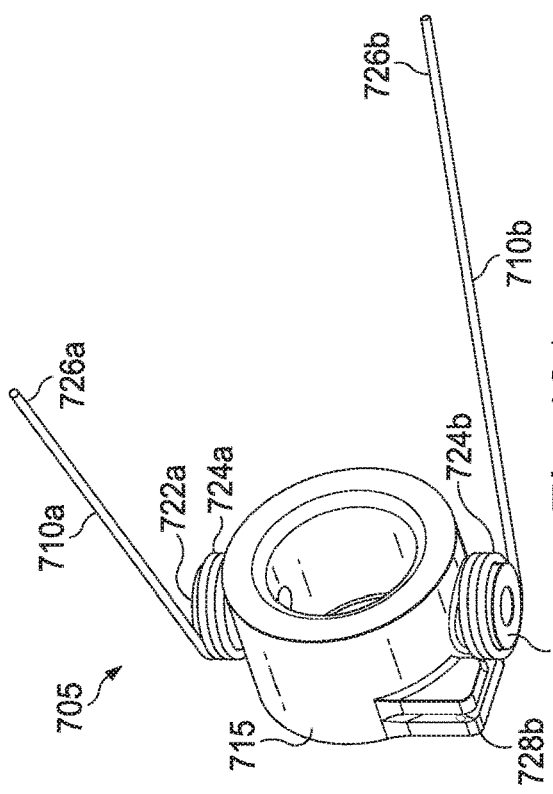
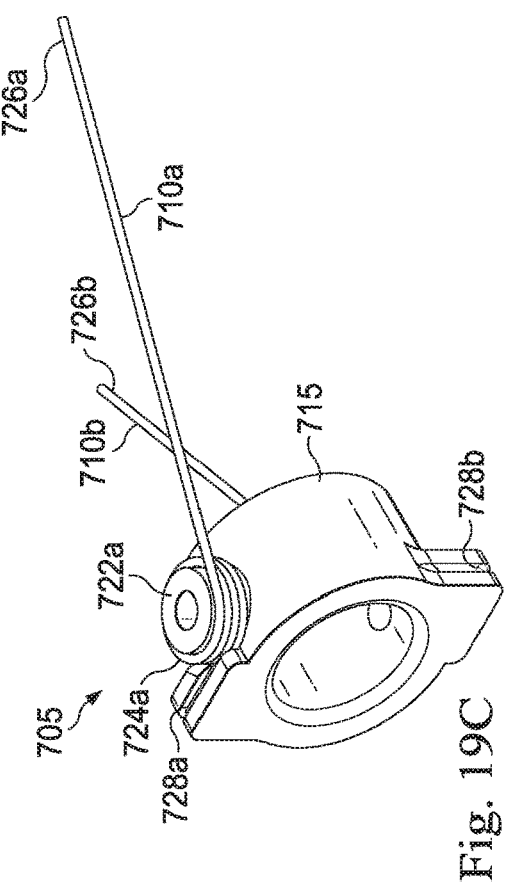
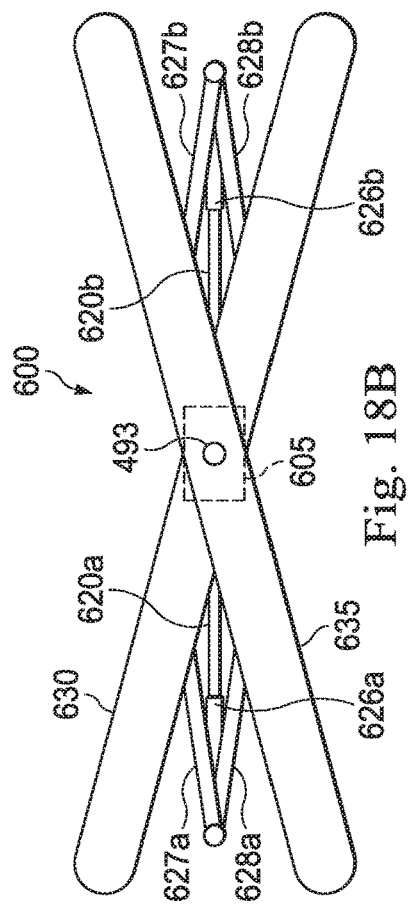
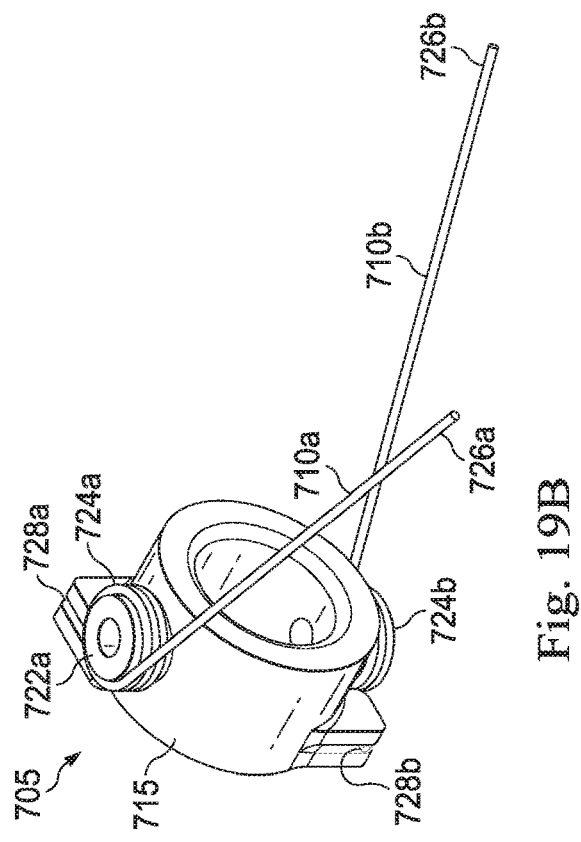
Fig. 18B
Fig. 19A
Fig. 19B
Fig. 19C

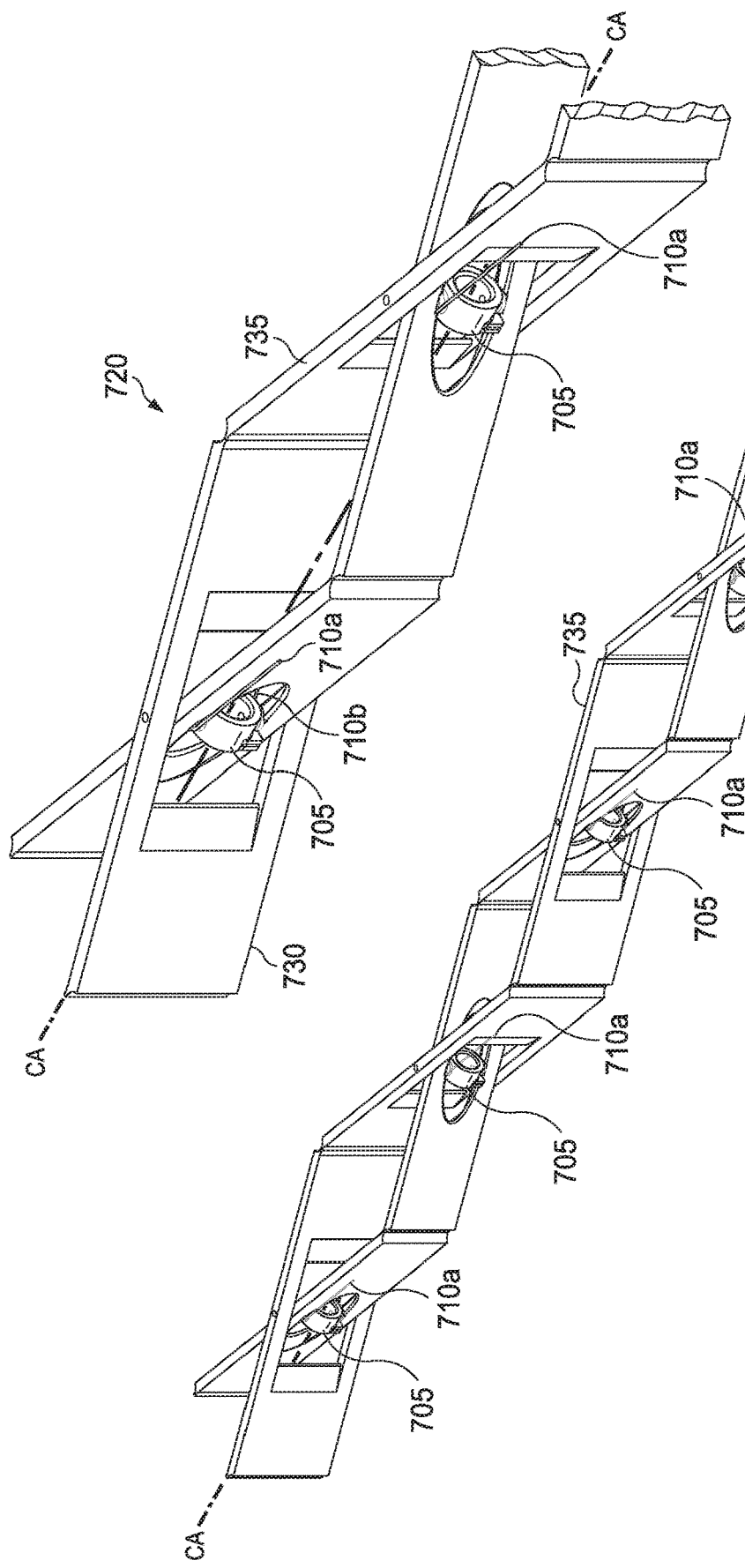

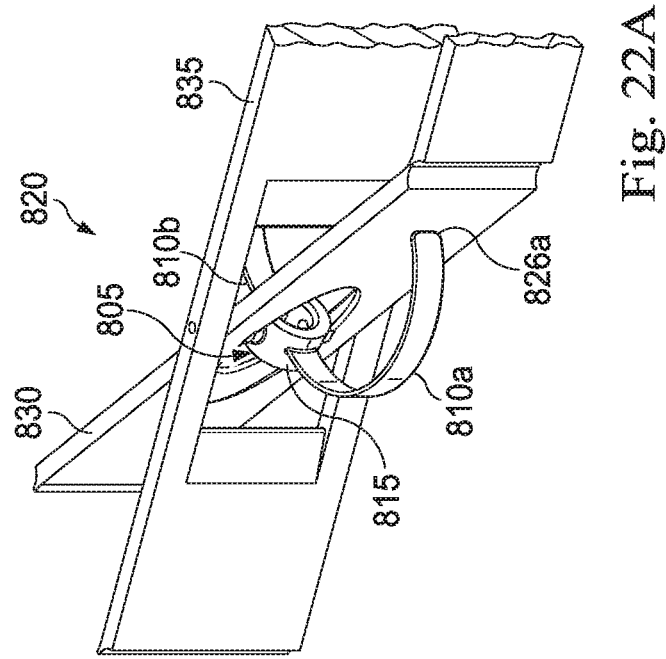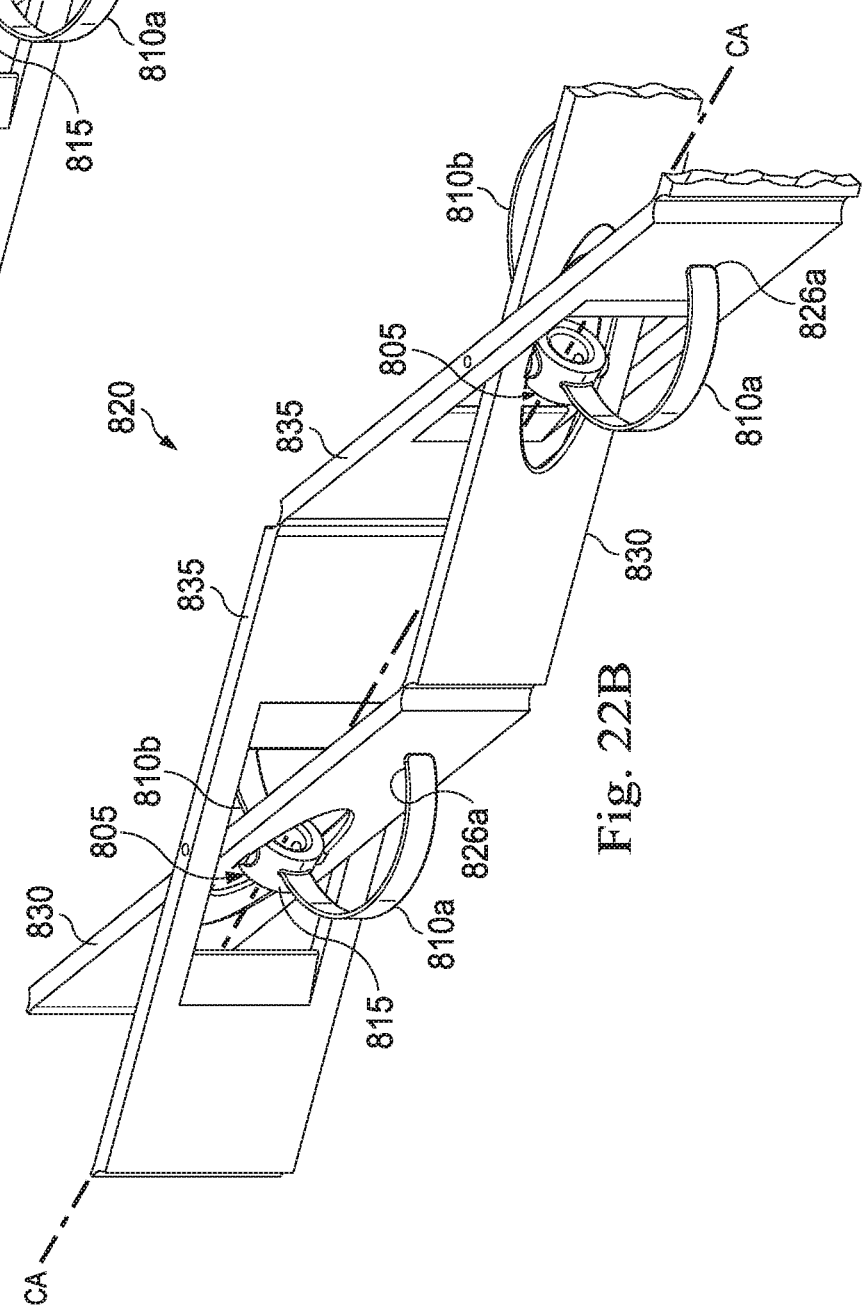

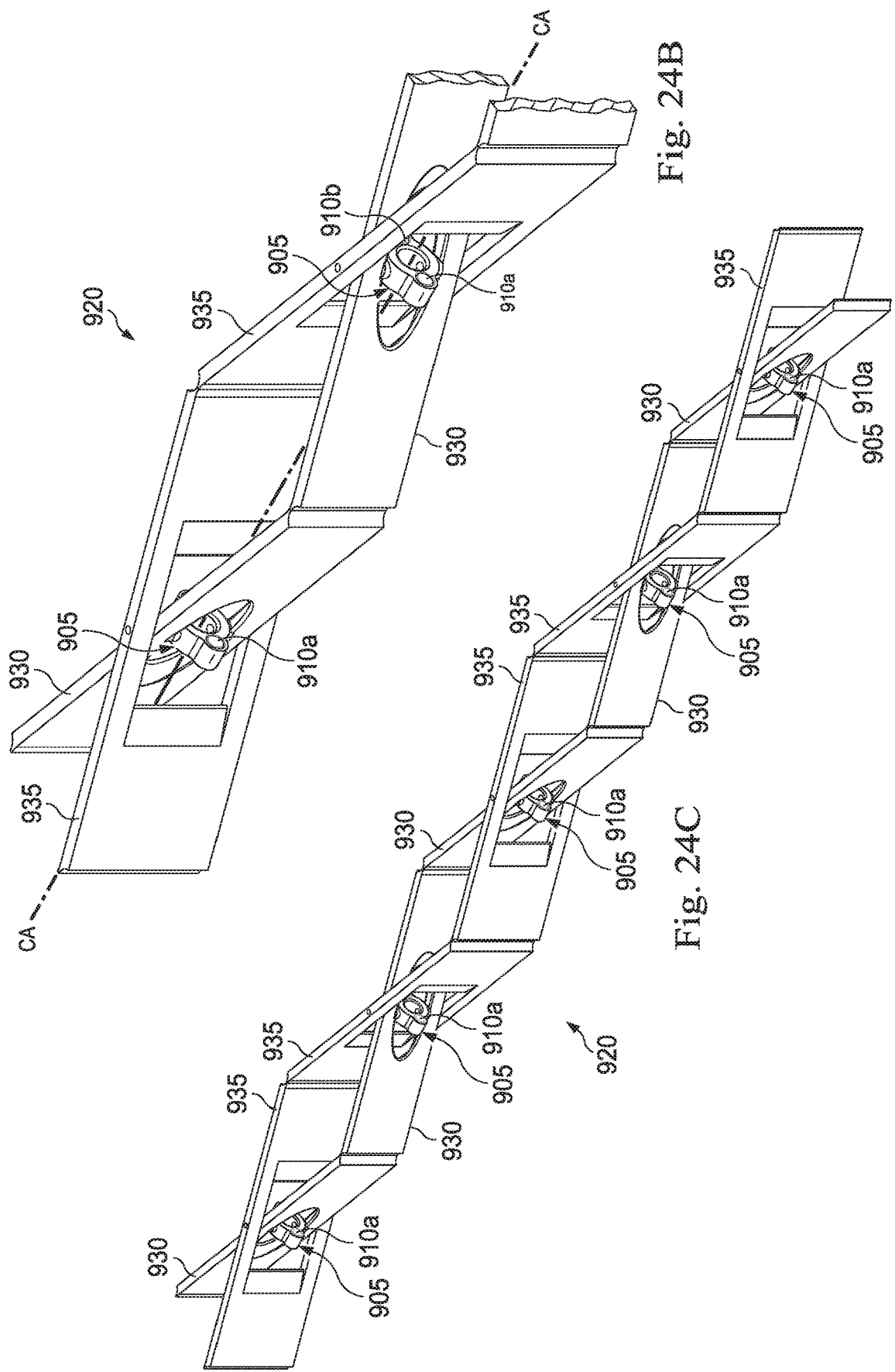

GUIDE APPARATUS FOR DELIVERY OF AN ELONGATE DEVICE AND METHODS OF USE

RELATED APPLICATIONS

This patent application is the U.S. national phase of International Application No. PCT/US2017/041160, filed Jul. 7, 2017, which designated the U.S. and claims priority to and the benefit of the filing date of U.S. Provisional Patent Application 62/359,957, entitled "GUIDE APPARATUS FOR DELIVERY OF AN ELONGATE DEVICE AND METHODS OF USE," filed Jul. 8, 2016, all of which are incorporated by reference herein in their entirety.

FIELD

The present disclosure is directed to systems and methods for navigating a patient anatomy to conduct a minimally invasive procedure, and more particularly to apparatus and methods for guiding and supporting the delivery of an elongate device (such as a flexible interventional instrument and/or a steerable interventional instrument) into a patient anatomy.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. Physicians may insert minimally invasive medical instruments (including surgical, diagnostic, therapeutic, or biopsy instruments) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. To reach the target tissue location, a minimally invasive interventional instrument may navigate natural or surgically created passageways in anatomical systems such as the lungs, the colon, the intestines, the kidneys, the heart, the circulatory system, or the like. Control of such an elongate device by medical personnel involves the management of several degrees of freedom including at least the management of insertion and retraction of the elongate device as well as steering of the device. In addition, different modes of operation may also be supported.

Teleoperational interventional systems may be used to insert the flexible interventional instruments into the patient anatomy. Several interventional instruments are made of flexible material that allows for maneuverability through a patient's body. In existing systems, at least a portion of the interventional instrument extending between the patient and a teleoperational manipulator is unsupported, and the flexible nature of the instrument can cause it to bend, twist, or buckle in an undesirable manner at a point external to the patient's body when force is exerted to insert the instrument into the patient's anatomy. Deformation of the instrument may damage internal components such as optical fiber shape sensors or endoscopic equipment. Improved systems and methods are needed for guiding and supporting interventional instruments as they are inserted into a patient anatomy to prevent instrument deformation.

SUMMARY

The embodiments of the invention are summarized by the claims that follow the description.

Consistent with some embodiments, An apparatus for guiding an elongated flexible instrument comprises a variable-length support assembly. The variable-length support assembly includes a first end, a second end, a plurality of support member pairs, and a plurality of eyelets configured to receive the elongated flexible instrument. Each support member pair comprises a first support member linked to a second support member, and each of the plurality of eyelets is movably coupled to at least one of the plurality of support member pairs along a longitudinal central axis between the first end and the second end. The variable-length support assembly is configured to selectively transition from a compressed configuration to an expanded configuration along the longitudinal central axis, and the plurality of eyelets are adapted to support the elongated flexible instrument as the elongated flexible instrument is advanced along the longitudinal central axis. Each of the plurality of eyelets includes a tapered alignment member configured to contact a tapered alignment member of an adjacent eyelet to move the plurality of eyelets into alignment along the longitudinal axis as the variable length assembly transitions from the expanded configuration to the compressed configuration.

Consistent with some embodiments, an apparatus for guiding an elongated flexible instrument comprises a variable-length support assembly. The variable-length support assembly includes a first end, a second end, a plurality of support member pairs, and a plurality of eyelets configured to receive the elongated flexible instrument. Each support member pair comprises a first support member linked to a second support member, and each of the plurality of eyelets is movably coupled to at least one of the support member pairs along a longitudinal central axis between the first end and the second end. The apparatus also includes a proximal coupler at the first end of the variable-length support assembly. The proximal coupler is configured to couple the variable-length support assembly to an instrument interface portion, and a proximal arm synchronizing assembly stabilizes a connection between the proximal coupler and the variable-length support assembly. The variable-length support assembly is configured to selectively transition from a compressed configuration to an expanded configuration along the longitudinal central axis. The plurality of eyelets are adapted to support the elongated flexible instrument as the elongated flexible instrument is advanced along the longitudinal central axis.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7 illustrates a top view of the instrument guiding apparatus shown in FIG. 4 in an expanded configuration.

FIG. 8 illustrates a bottom view of the instrument guiding apparatus shown in FIG. 4 in an expanded configuration.

FIG. 9 illustrates a perspective view of the instrument guiding apparatus shown in FIG. 4 in an expanded configuration.

FIGS. 10A-10D illustrate perspective views of an exemplary arm synchronizing assembly coupled to the variable-length support assembly, and FIG. 10E illustrates a top view of the exemplary arm synchronizing assembly according to one embodiment of the present disclosure.

Figure 11A:
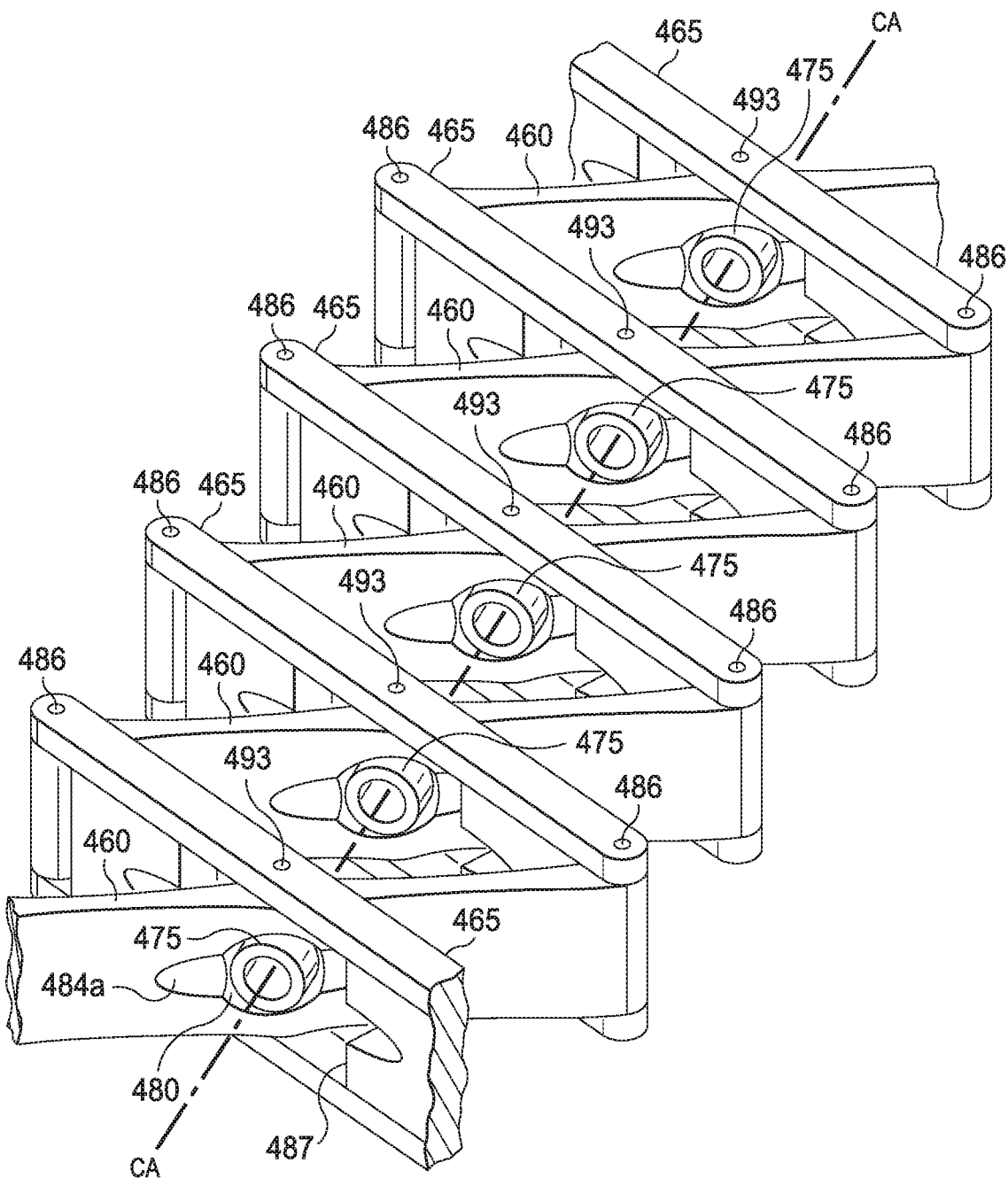
FIG. 11A illustrates a perspective view of a central portion of the variable-length support assembly according to one embodiment of the present disclosure.
Figure 11B:
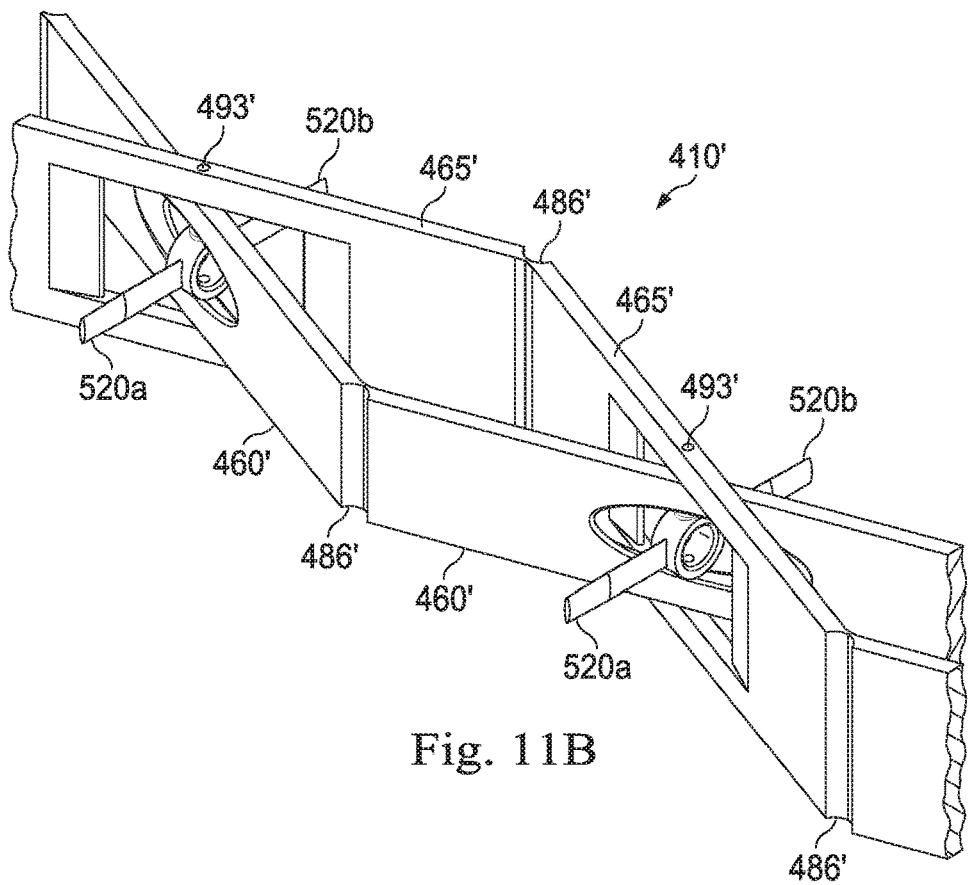
Figure 11D:
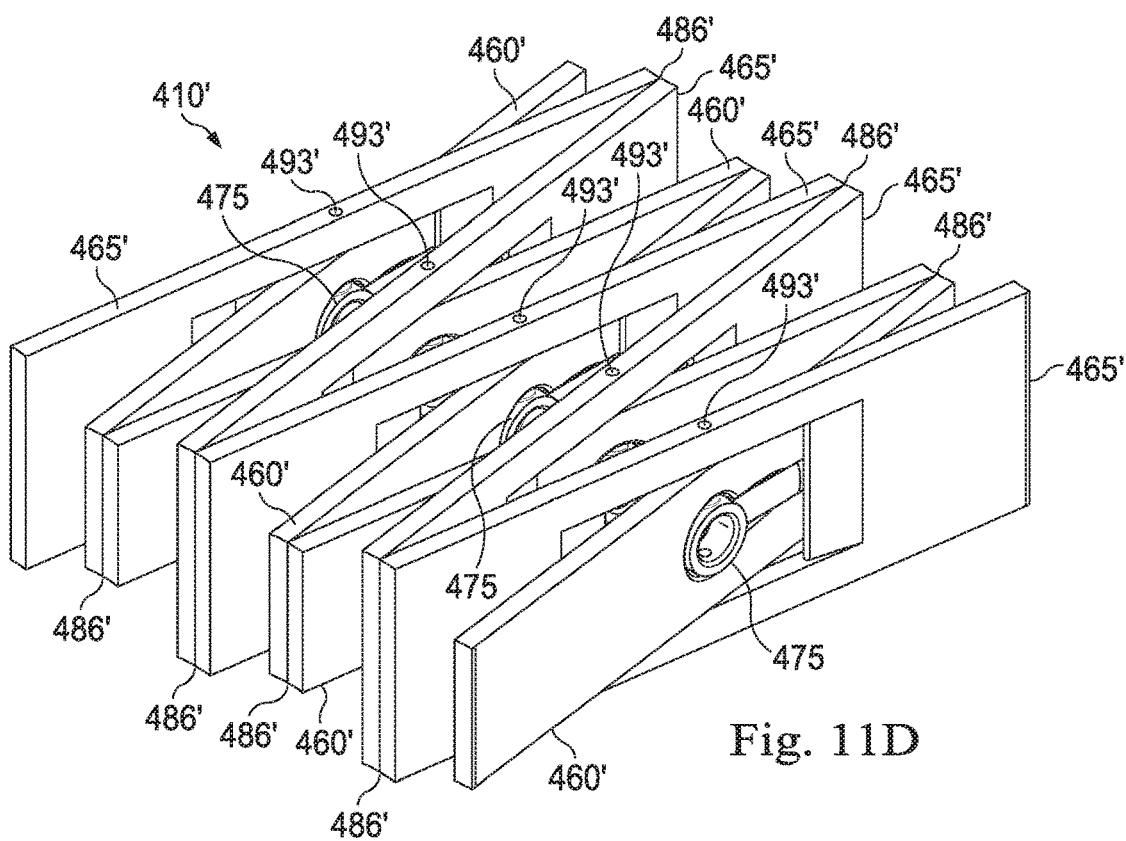

FIGS. 11B-11D illustrate perspective views of a central portion of an exemplary variable-length support assembly according to another embodiment of the present disclosure. FIG. 11B illustrates a close-up perspective view of exemplary support members linked by living hinges in an expanded configuration according to one embodiment of the present disclosure. FIG. 11C illustrates a perspective view of the variable-length support assembly in an expanded configuration according to one embodiment of the present disclosure. FIG. 11D illustrates a perspective view of the variable-length support assembly in a compressed configuration according to one embodiment of the present disclosure.

FIG. 12 illustrates a perspective view of an exemplary first support member and an exemplary eyelet according to one embodiment of the present disclosure.

Figure 13:
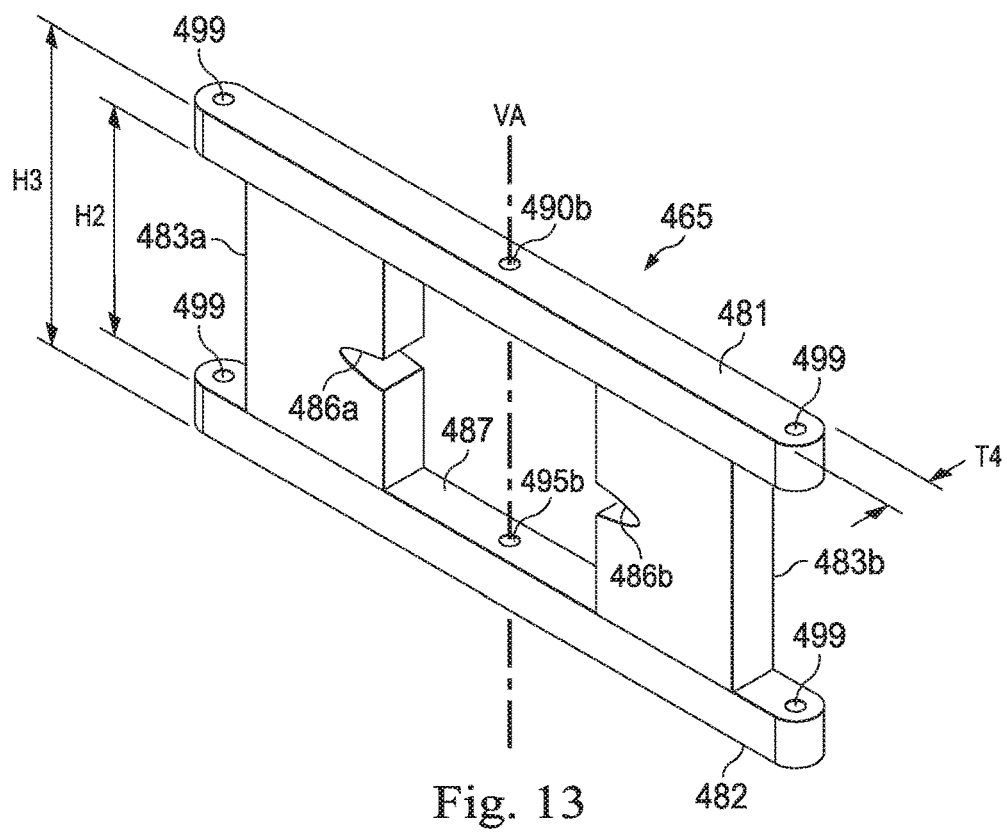

FIG. 13 illustrates a perspective view of an exemplary second support member according to one embodiment of the present disclosure.

Figure 14:
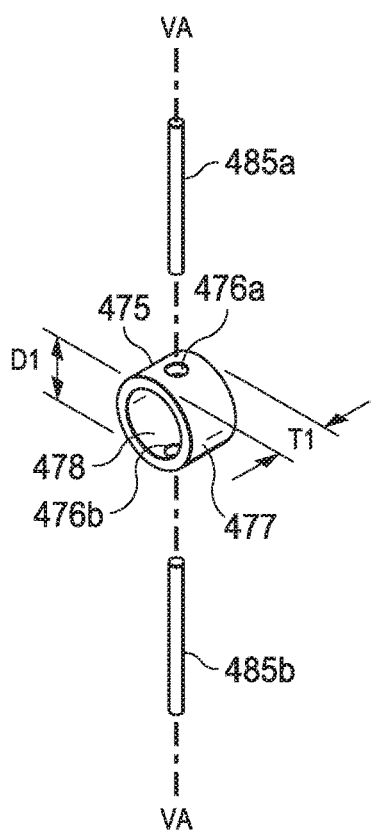

FIG. 14 illustrates a perspective view of the eyelet shown in FIG. 12 and exemplary pins according to one embodiment of the present disclosure.

Figure 15:
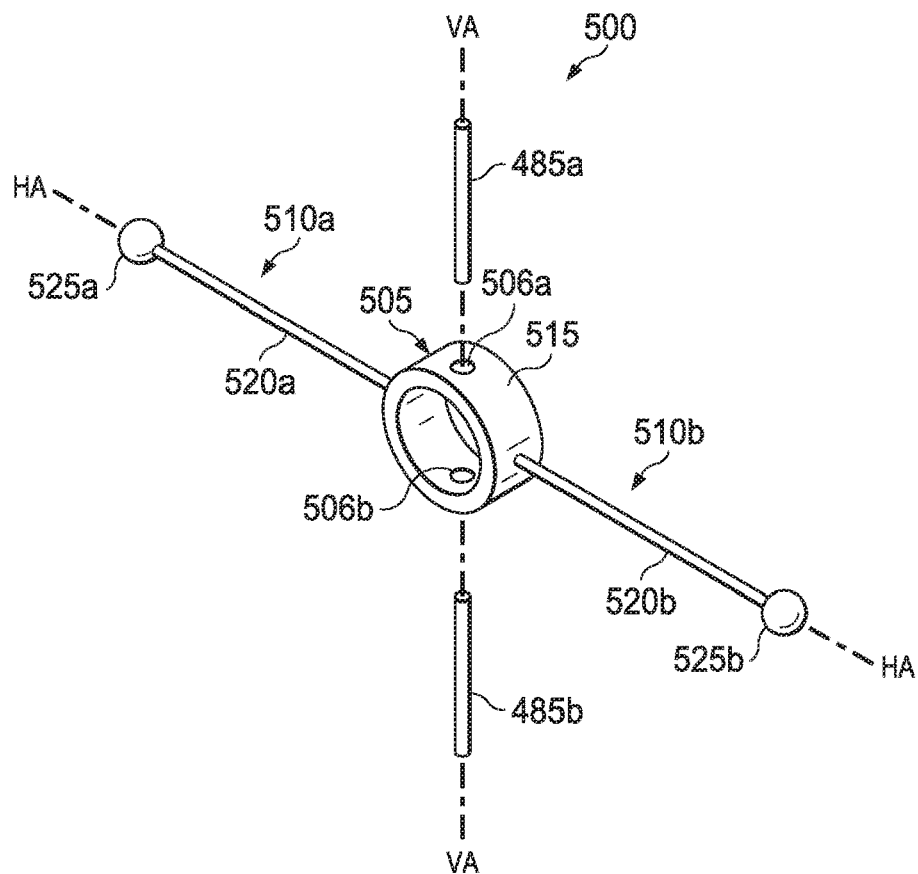
Figure 16A:
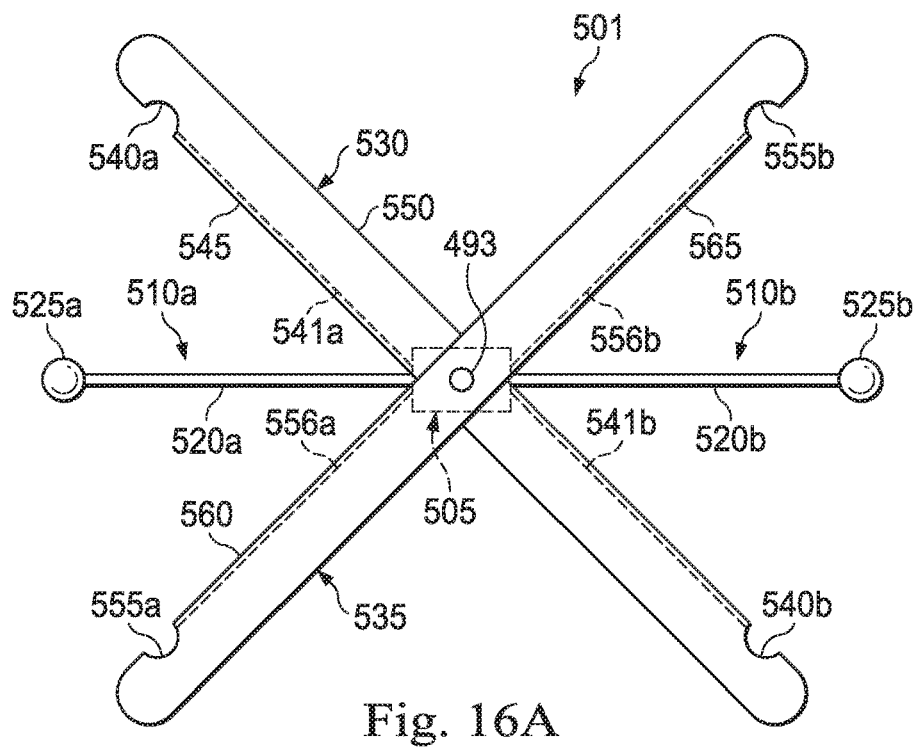
Figure 16B:
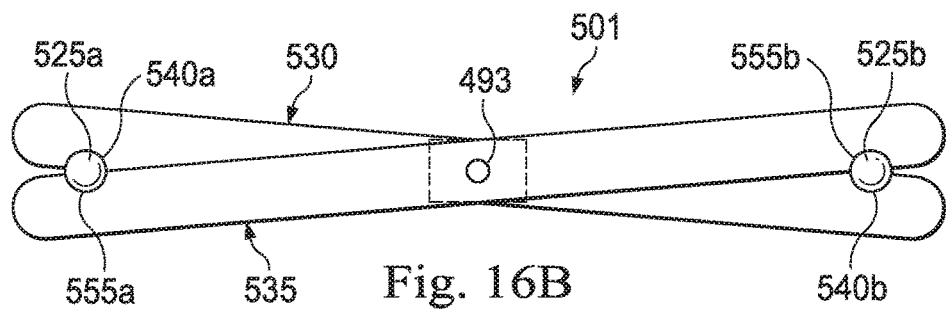

FIGS. 15-16B illustrate portions of an exemplary instrument guiding apparatus including exemplary alignment members according to one embodiment of the present disclosure. In particular, FIG. 15 illustrates a perspective view of an exemplary eyelet, exemplary pins, and exemplary alignment members. FIG. 16A illustrates a top cutaway view of the eyelet and the alignment members shown in FIG. 15 coupled to a first support member and a second support member in an expanded configuration. FIG. 16B illustrates a top cutaway view of the eyelet and the alignment members shown in FIG. 15 coupled to the first and second support members in a compressed configuration.

Figure 17:
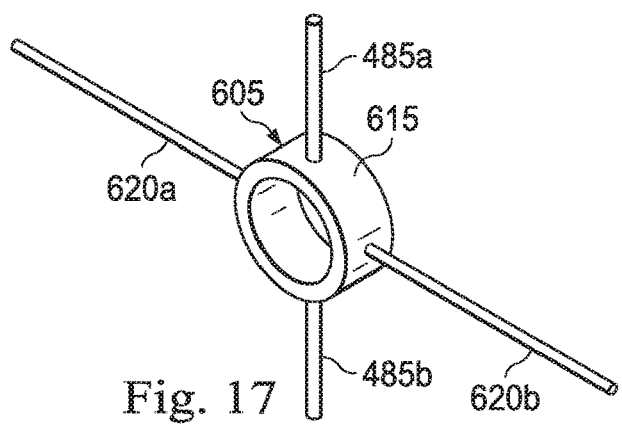
Figure 18A:
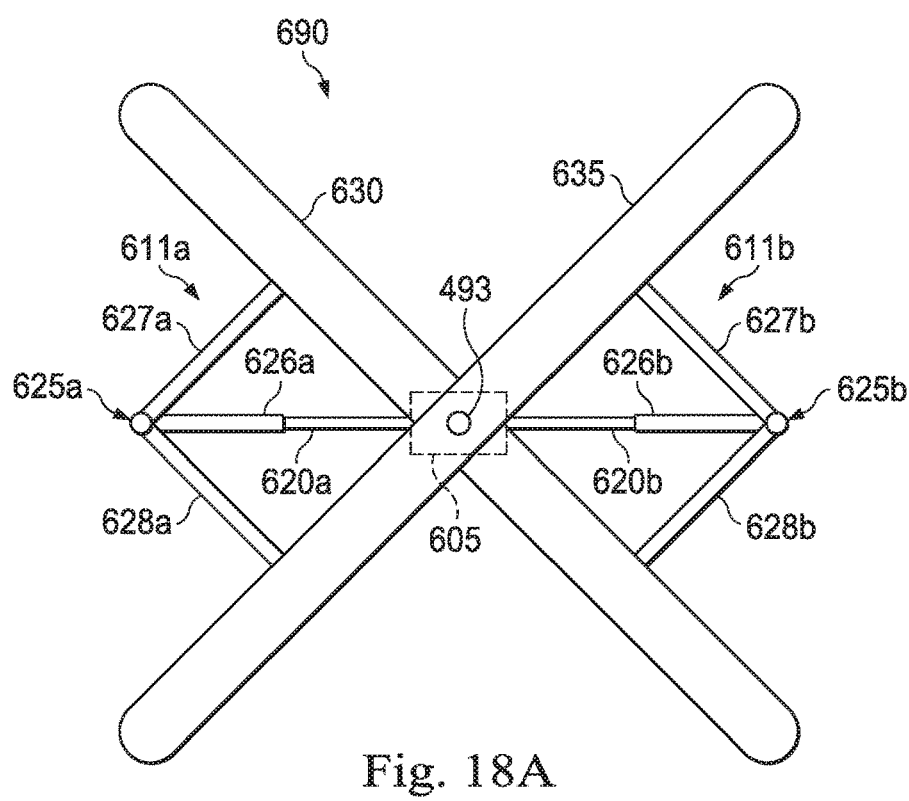
Figure 20A:
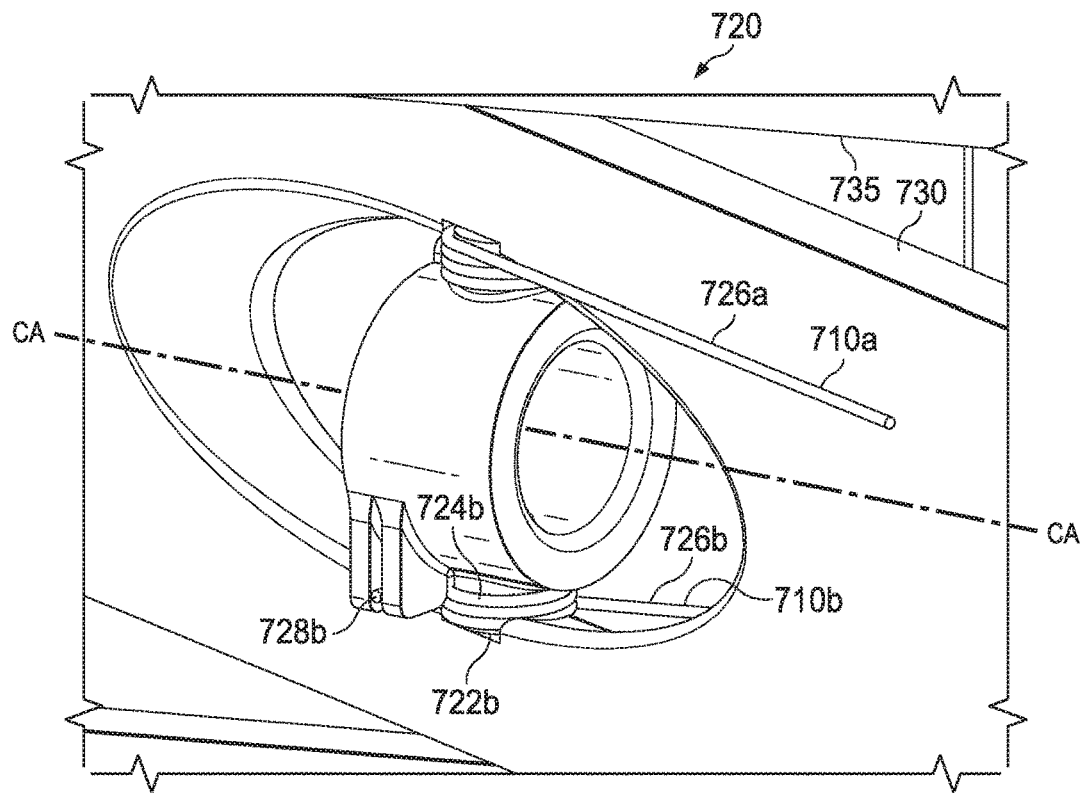
Figure 20B:
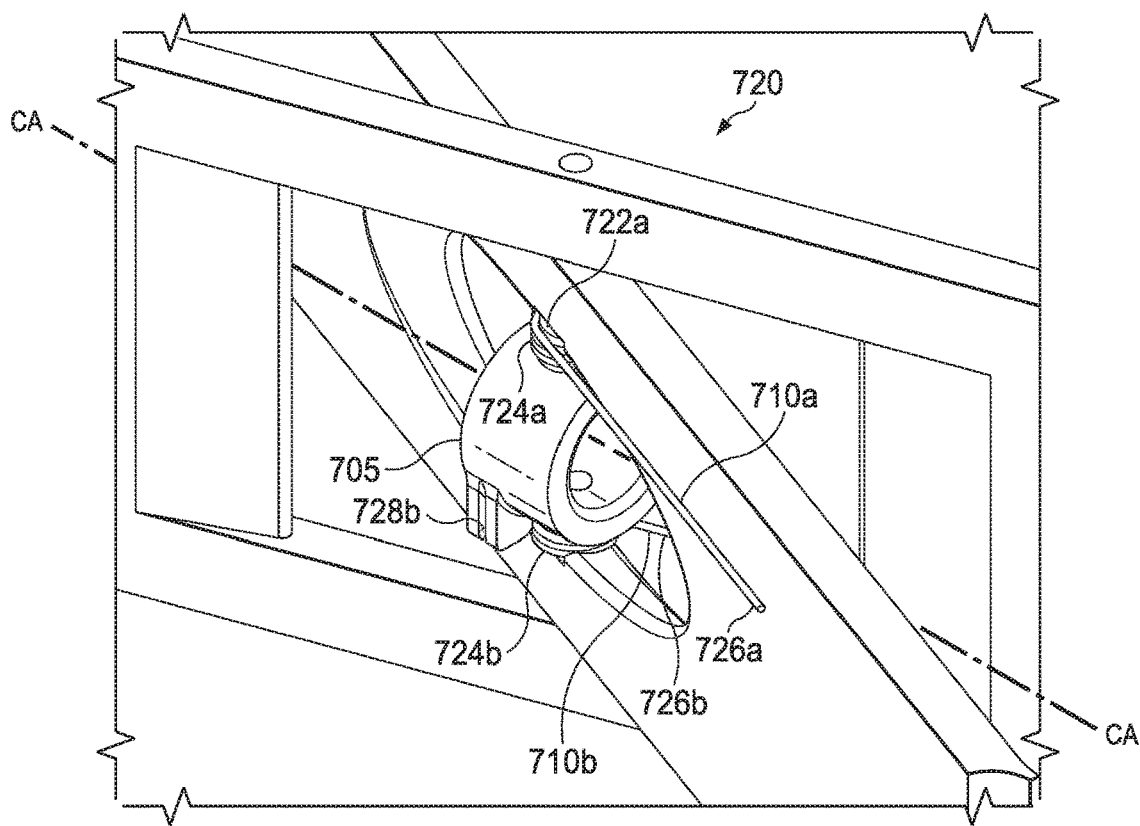

FIGS. 17-18B illustrate portions of an exemplary instrument guiding apparatus including exemplary alignment members according to another embodiment of the present disclosure. In particular, FIG. 17 illustrates a perspective view of an exemplary eyelet and exemplary alignment members. FIG. 18A illustrates a top view of the eyelet and the alignment members shown in FIG. 17 coupled to a first support member and a second support member in an expanded configuration. FIG. 18B illustrates a top view of the eyelet and the alignment members shown in FIG. 17 coupled to the first and second support members in a partially compressed configuration.

FIGS. 19A-19C illustrate perspective views of an exemplary eyelet and exemplary alignment members according to one embodiment of the present disclosure.

FIGS. 20A-20D illustrate perspective views of an exemplary variable-length support assembly including the eyelet and alignment members shown in FIGS. 19A-19C according to one embodiment of the present disclosure.

Figure 21:
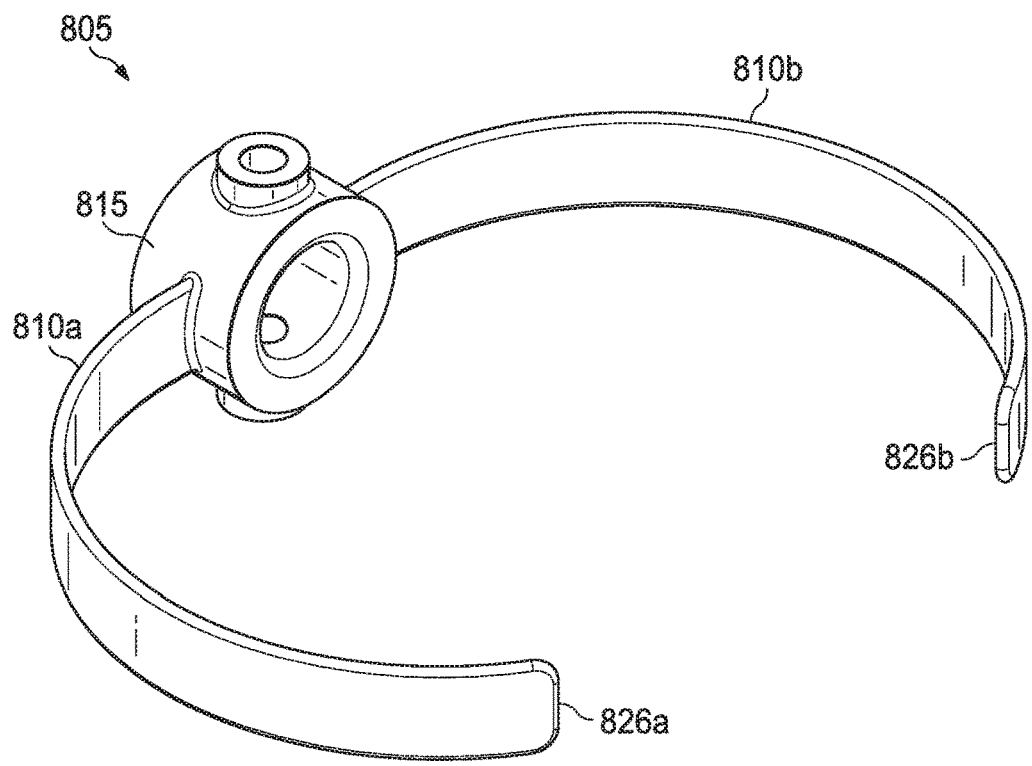

FIG. 21 illustrates a perspective view of an exemplary eyelet according to one embodiment of the present disclosure.

Figure 22C:
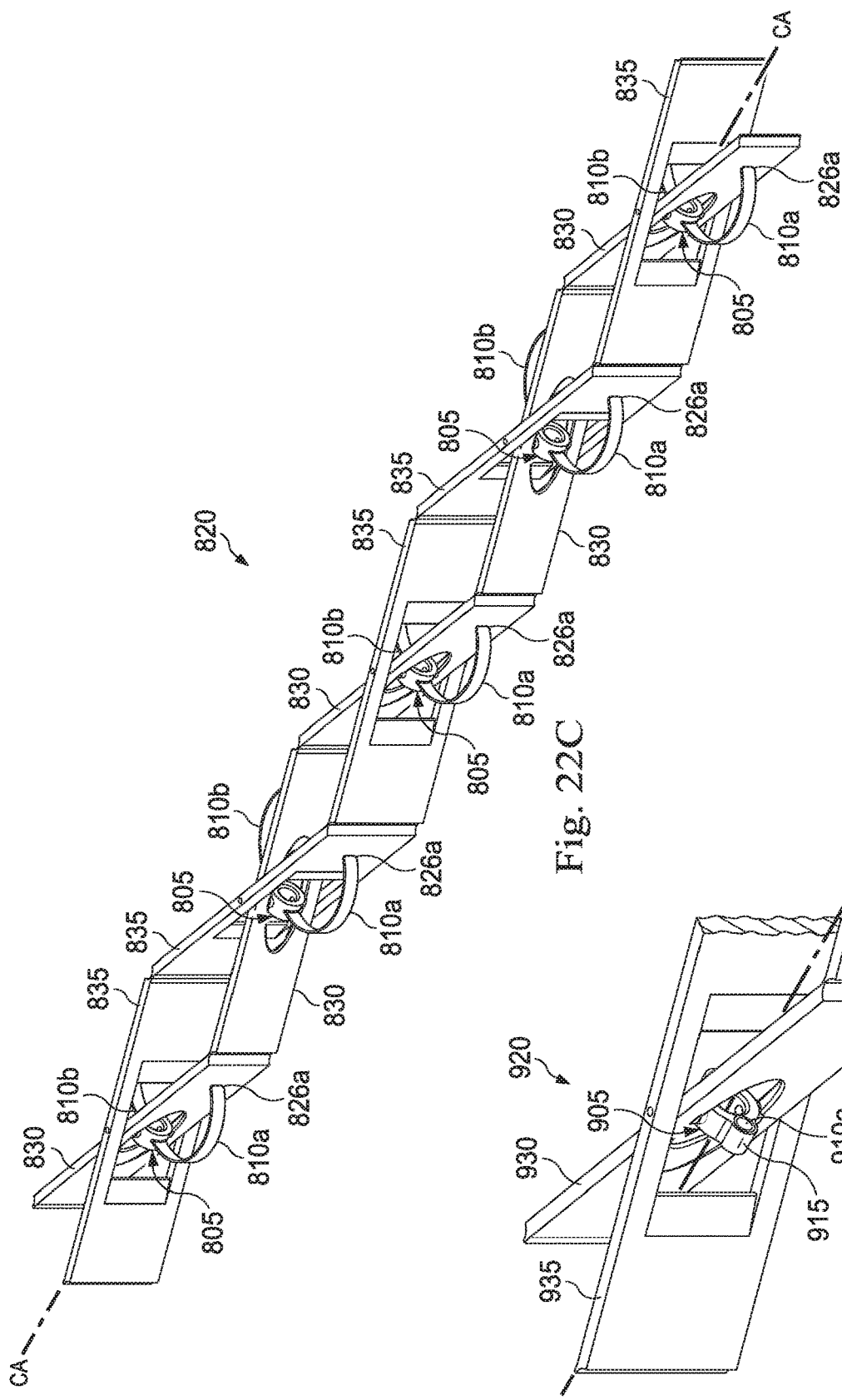

FIGS. 22A-22C illustrate perspective views of an exemplary variable-length support assembly including the eyelet shown in FIG. 21 according to one embodiment of the present disclosure.

Figure 23:
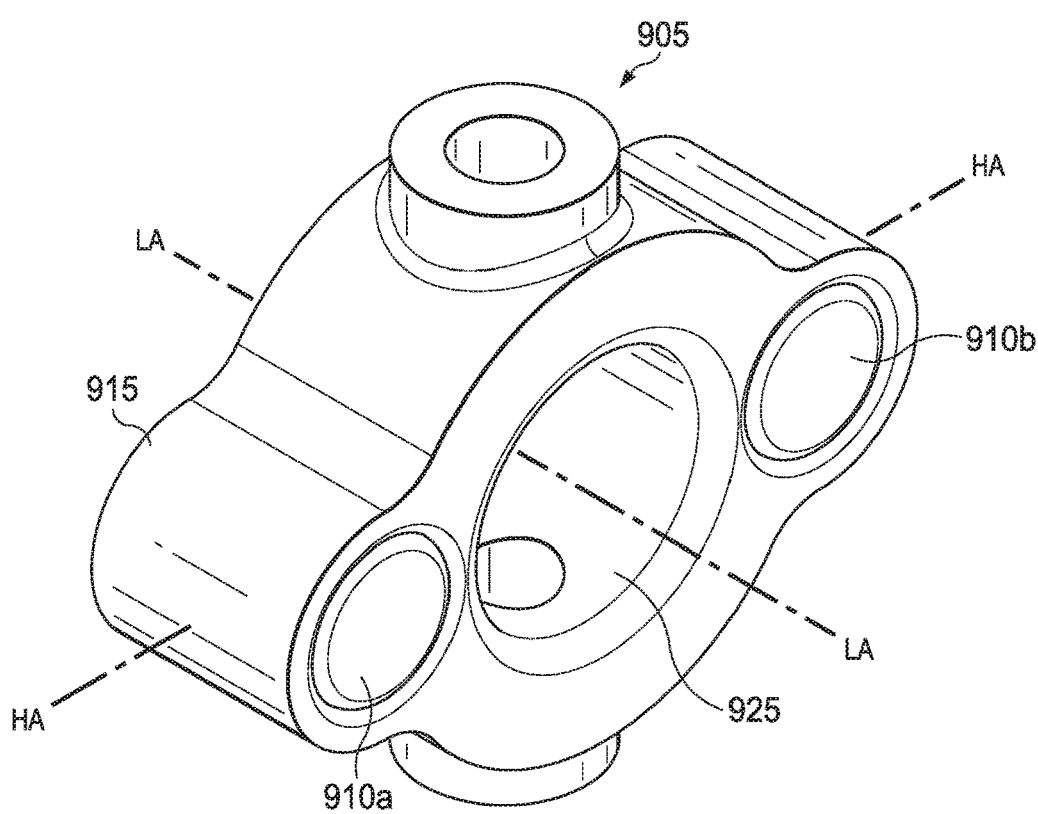

FIG. 23 illustrates a perspective view of an exemplary eyelet according to one embodiment of the present disclosure.

Figure 24A:
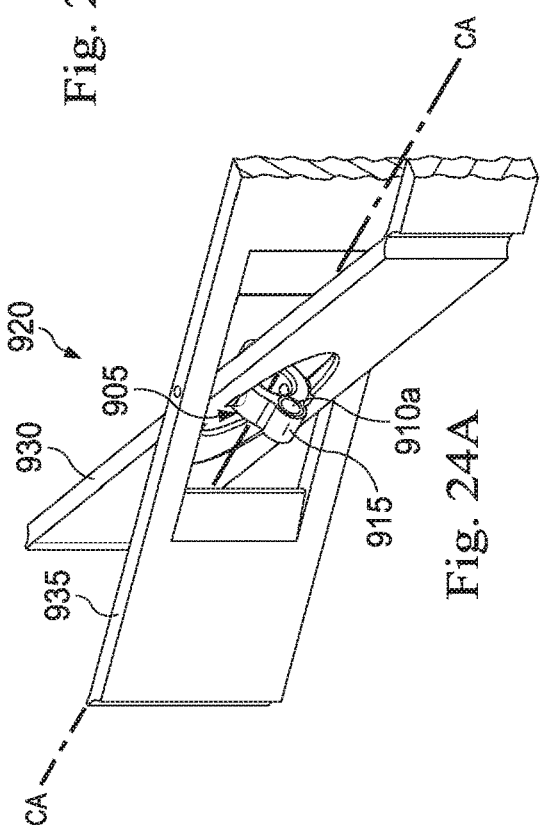

FIGS. 24A-24C illustrate perspective views of an exemplary variable-length support assembly including the eyelet shown in FIG. 21 according to one embodiment of the present disclosure.

Figure 25A:
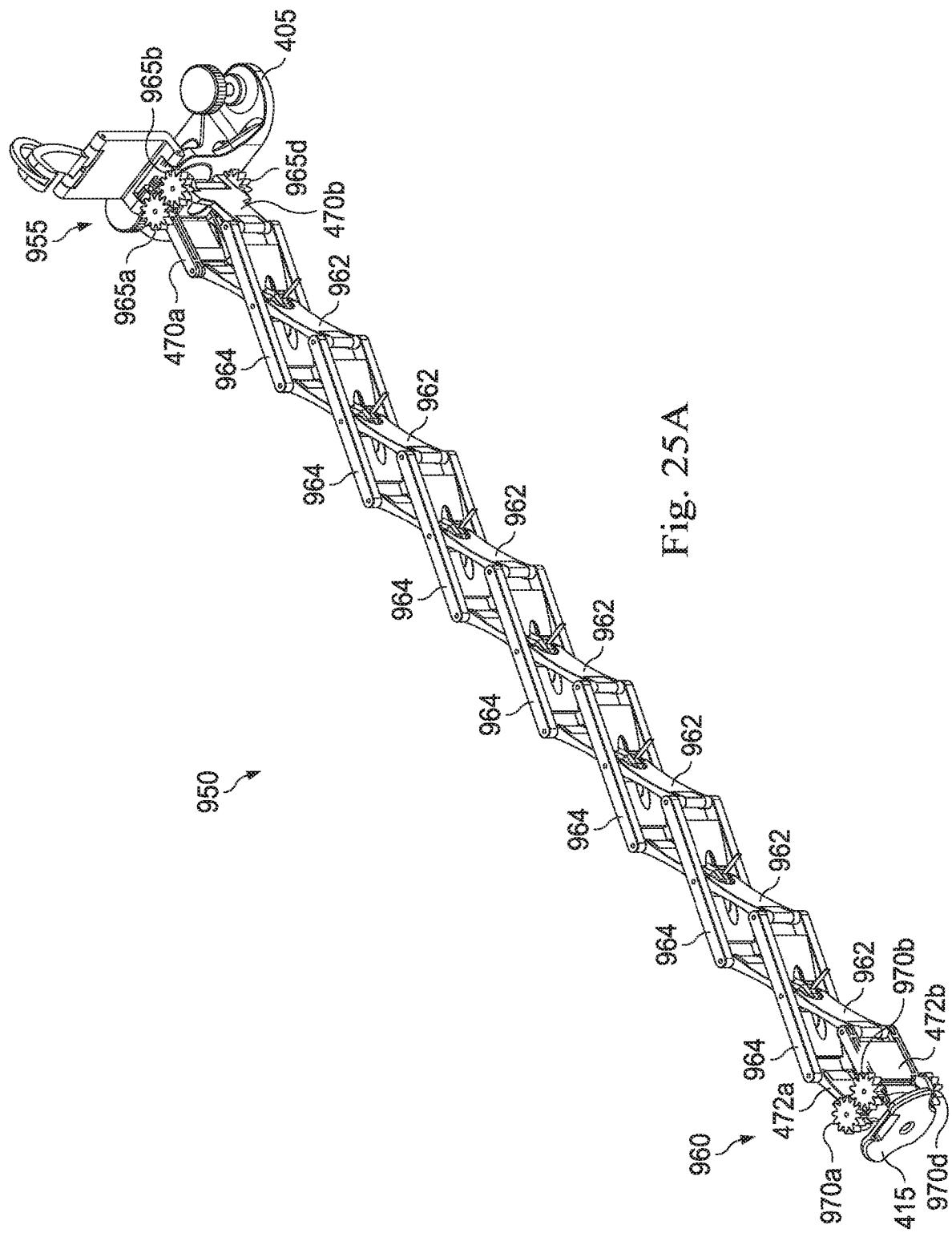
Figure 25B:
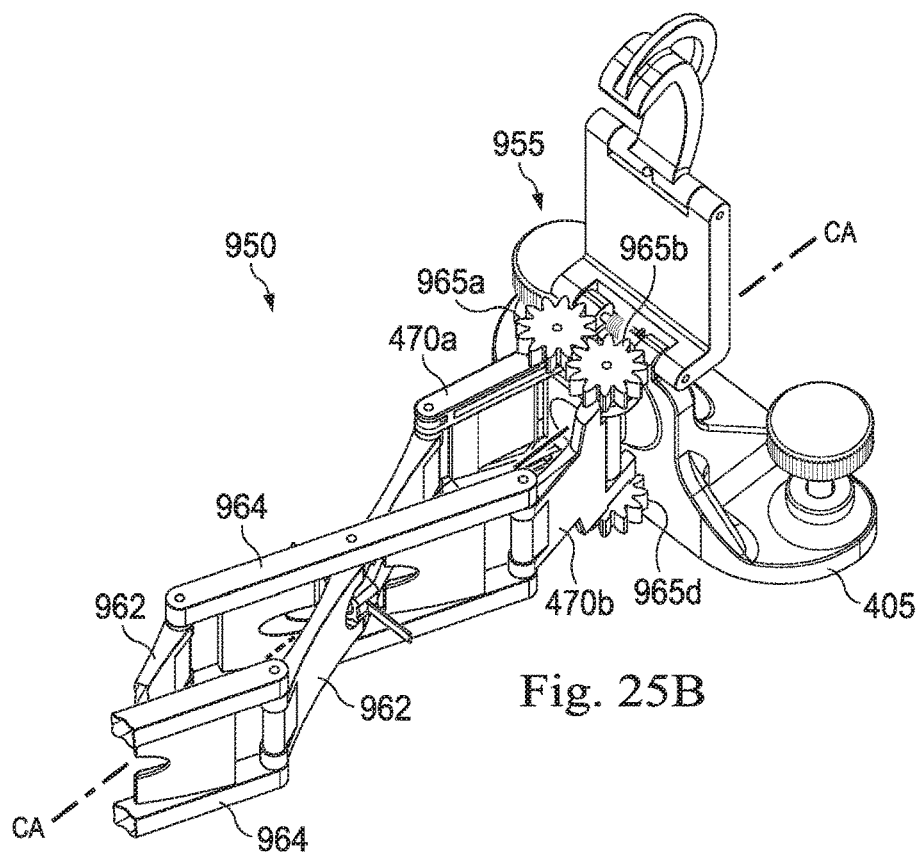
Figure 25C:
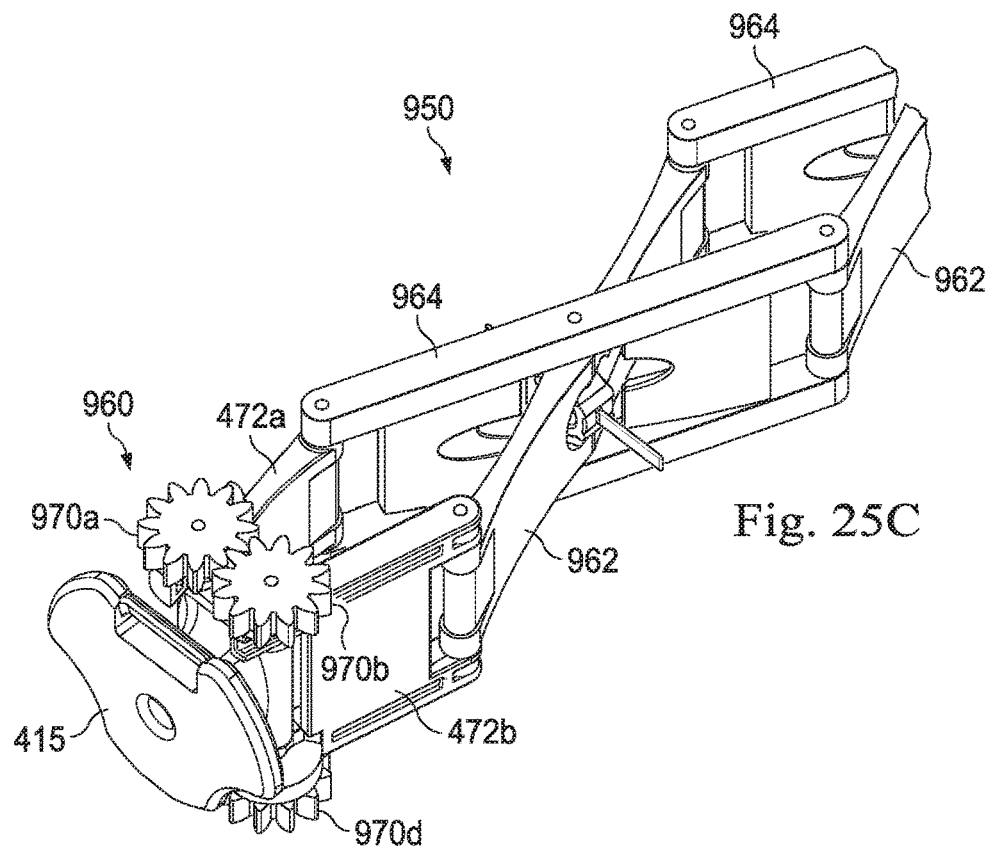

FIGS. 25A-25C illustrate perspective views of an exemplary variable-length support assembly coupled to exemplary arm synchronizing assemblies according to one embodiment of the present disclosure. FIG. 25A illustrates the length of the variable-length support assembly. FIG. 25B illustrates an exemplary proximal arm synchronizing assembly coupled to the variable-length support assembly, and FIG. 25C illustrates an exemplary distal arm synchronizing assembly according to one embodiment of the present disclosure.

Figure 2A:
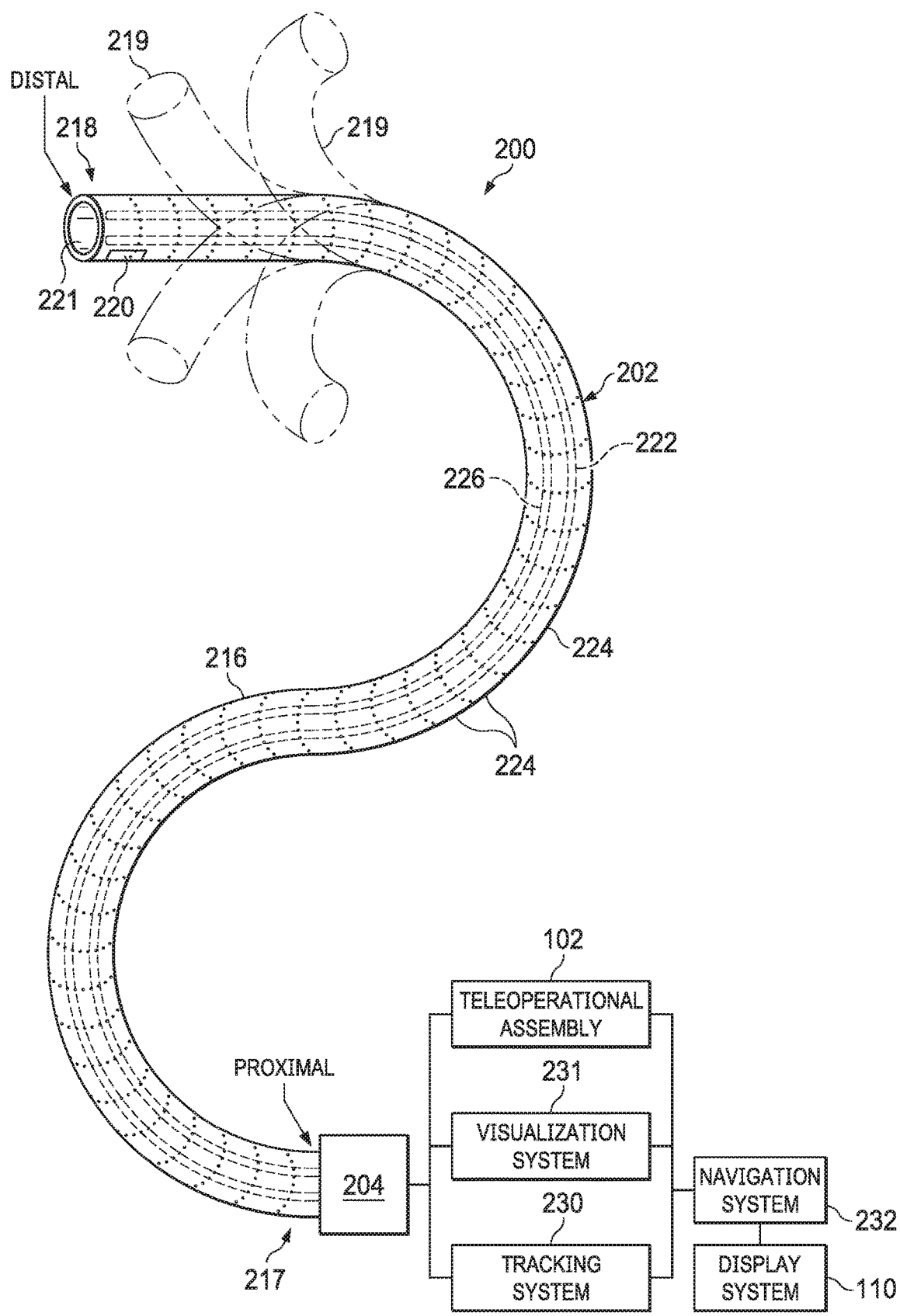
FIG. 2A is a simplified diagram of a medical instrument system according to some embodiments of the present disclosure.
Figure 2B:
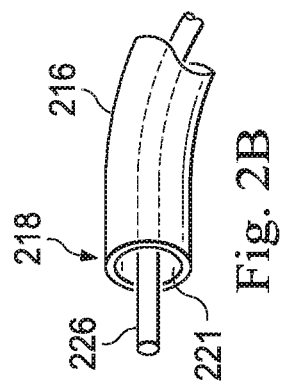
FIG. 2B is a simplified diagram of a medical instrument with an extended medical tool according to some embodiments of the present disclosure.
Figure 26A:
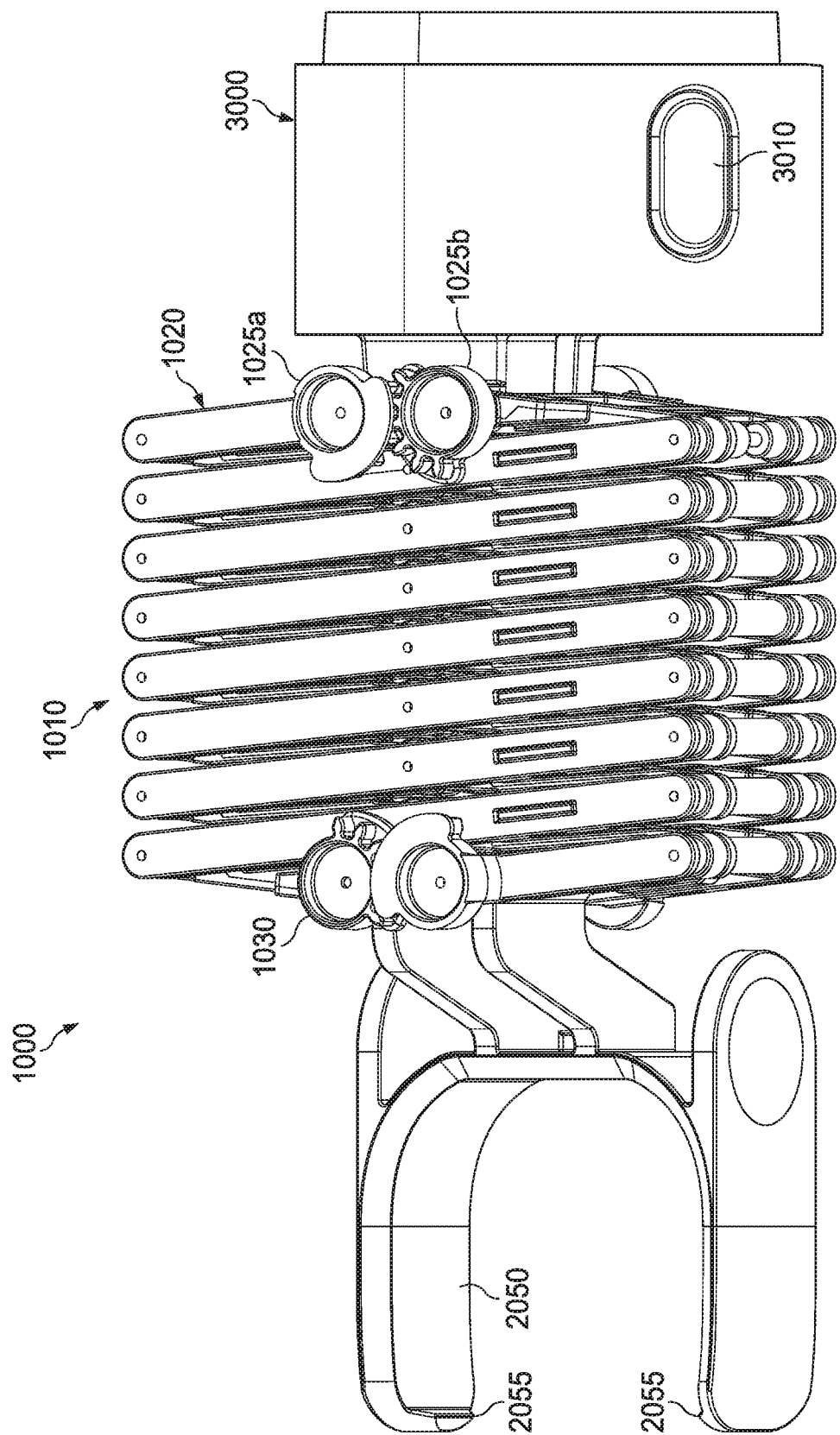

FIGS. 26A-2B illustrate perspective views of an exemplary instrument guiding apparatus according to another embodiment of the present disclosure.

Figure 27B:
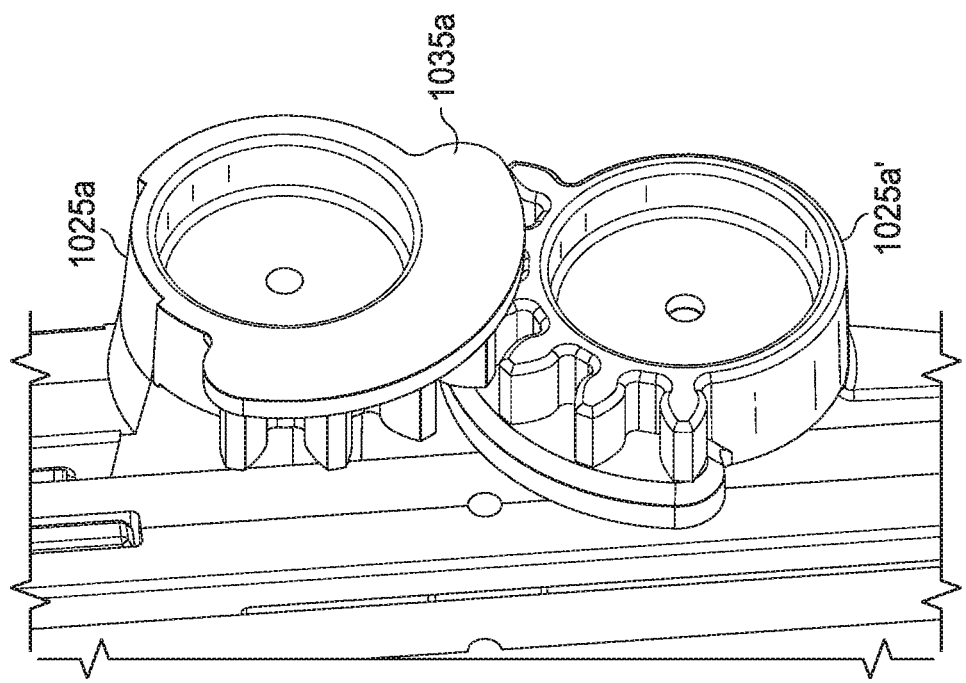
Figure 27A:
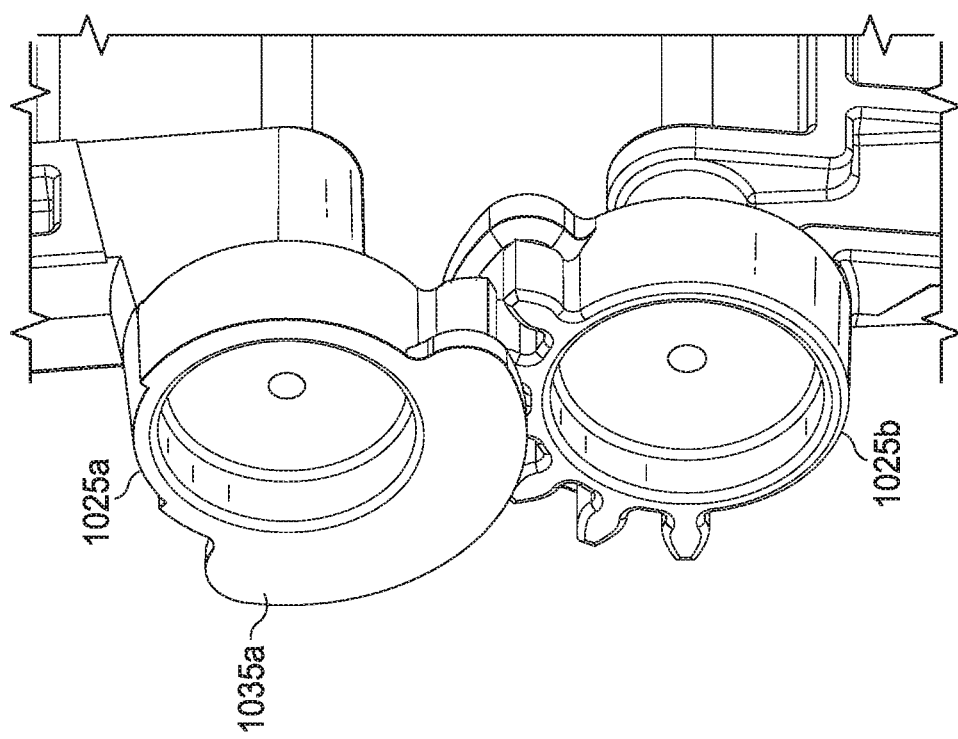

FIG. 27A illustrates a set of gears in a proximal arm synchronizing assembly according to an embodiment of the present disclosure.

FIG. 27B illustrates a set of gears in a proximal arm synchronizing assembly according to another embodiment of the present disclosure.

Figure 28:
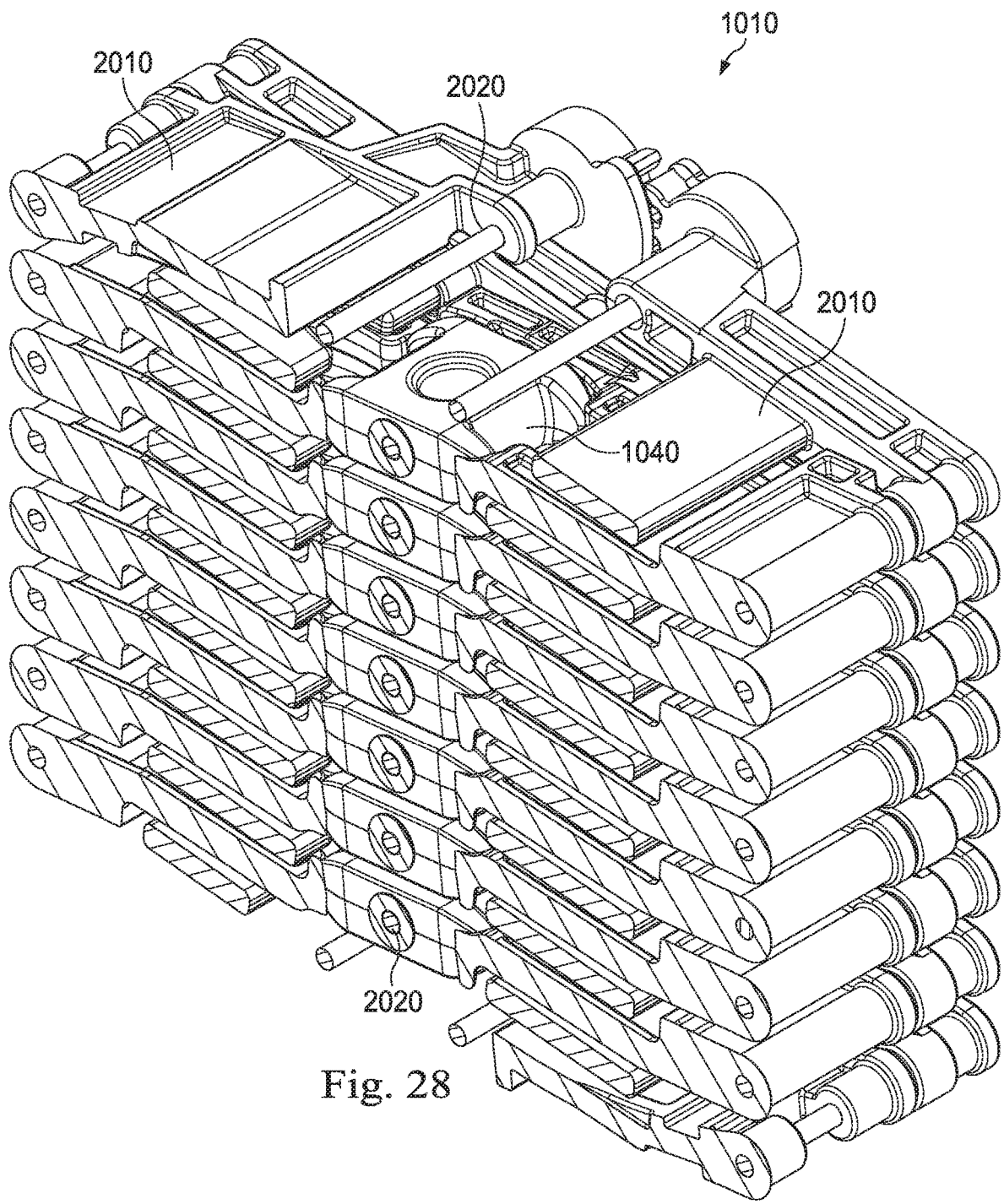

FIG. 28 illustrates a cross sectional view of the variable-length support assembly in a collapsed state.

Figure 29A:
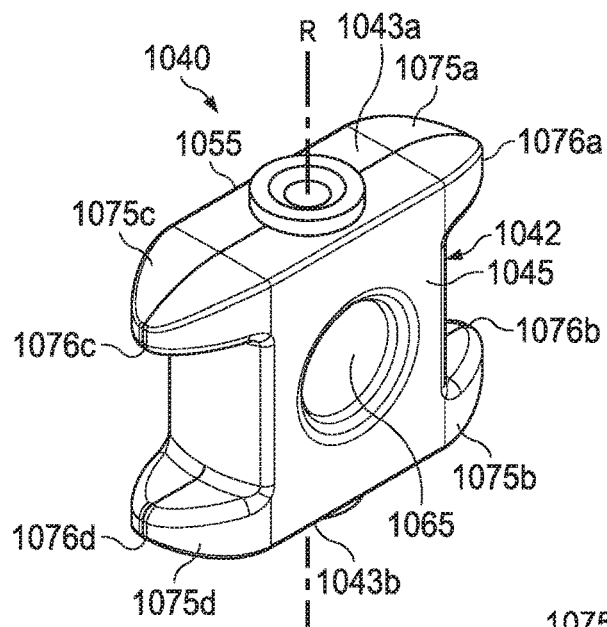
Figure 29B:
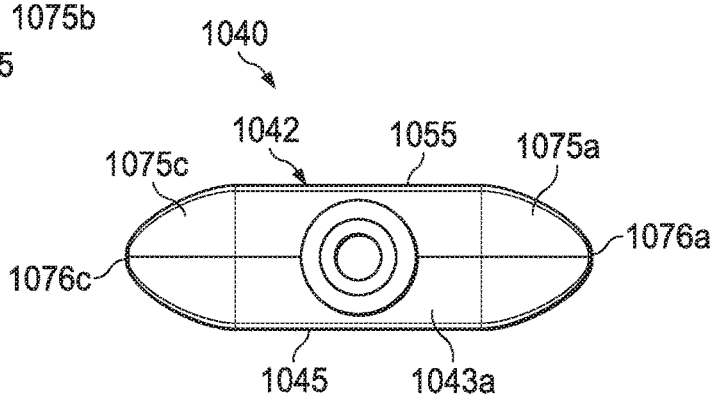

FIGS. 29A and 29B illustrate perspective and top views, respectively, of an eyelet according to an embodiment of the present disclosure.

Figure 30A:
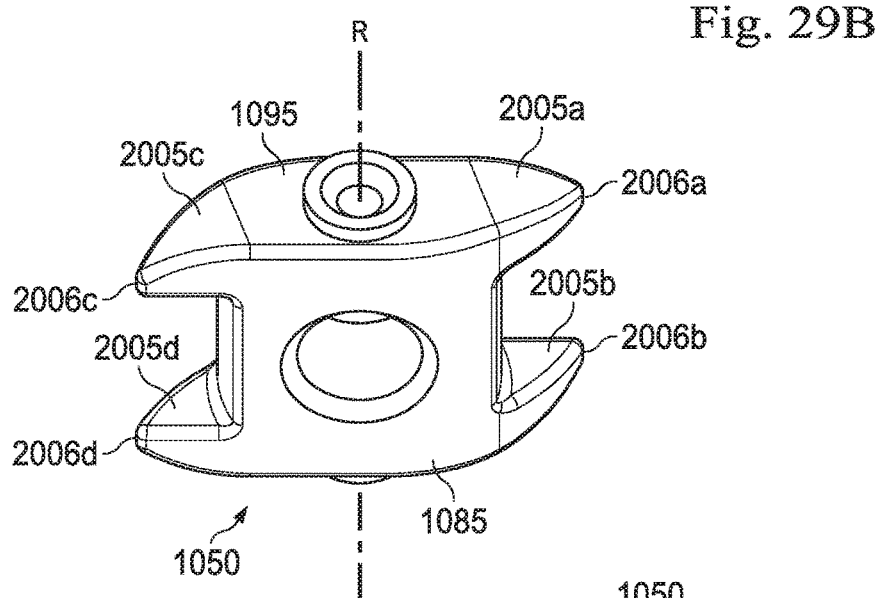
Figure 30B:
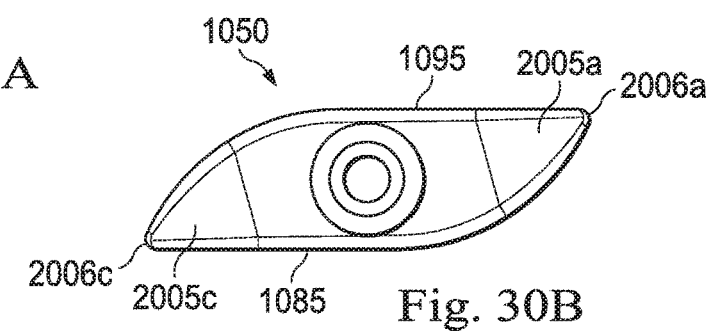

FIGS. 30A and 30B illustrate perspective and top views, respectively, of an eyelet according to another embodiment of the present disclosure.

Figure 31A:
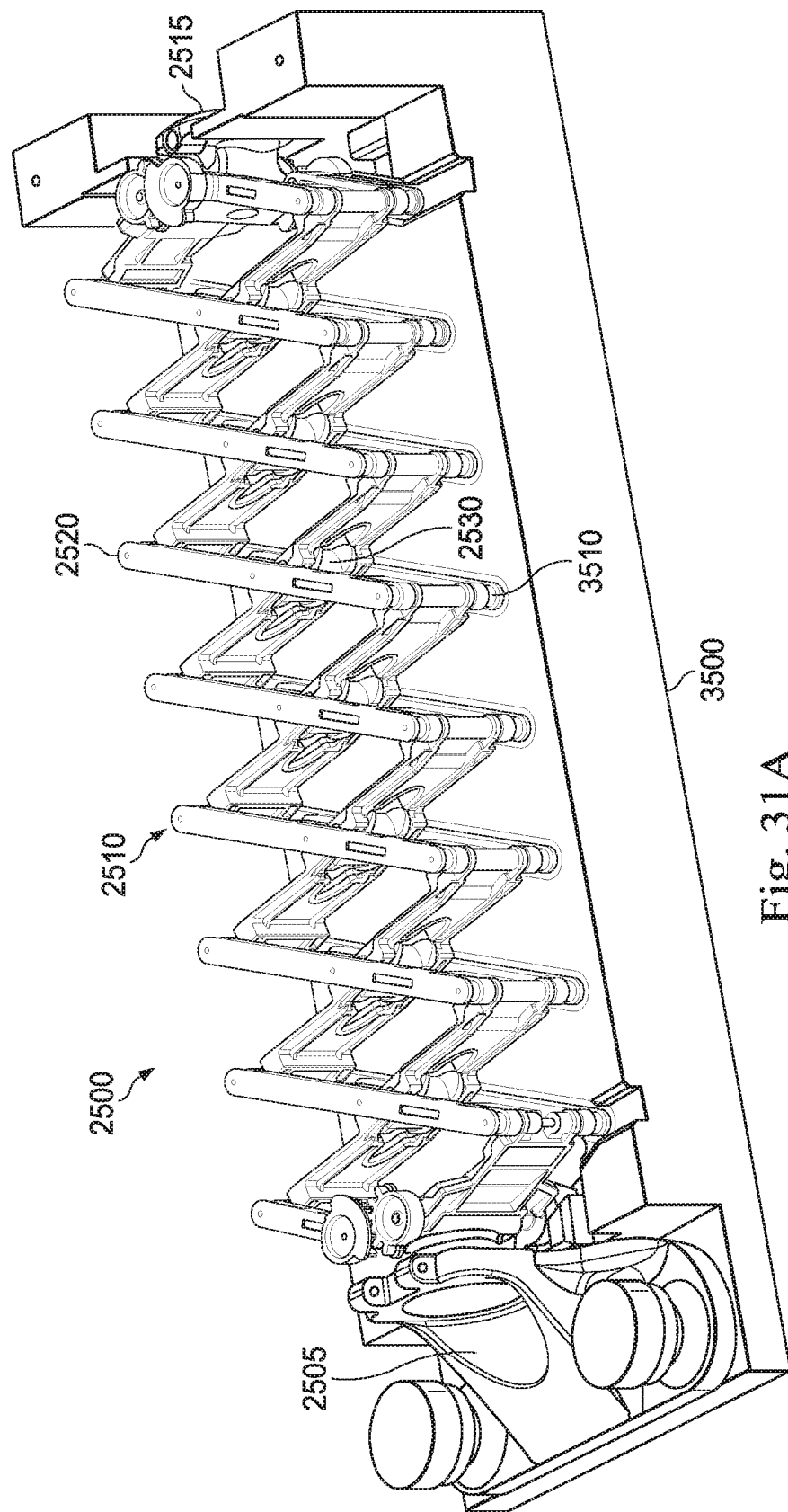
Figure 31B:
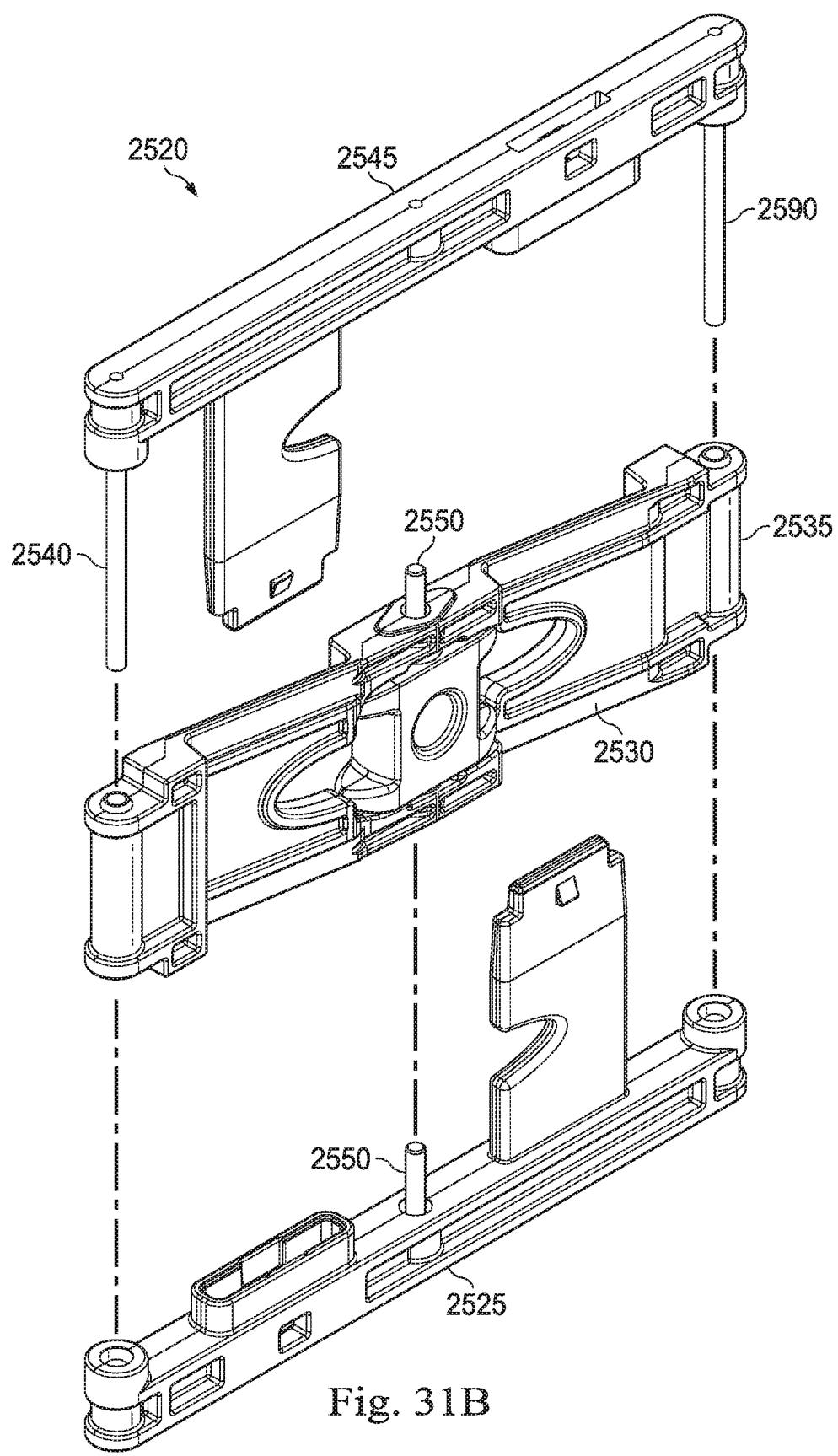

FIG. 31A illustrates an assembly fixture for assembly of an instrument guiding apparatus FIG. 31B illustrates a single support member 2520 in an exploded configuration.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set firth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
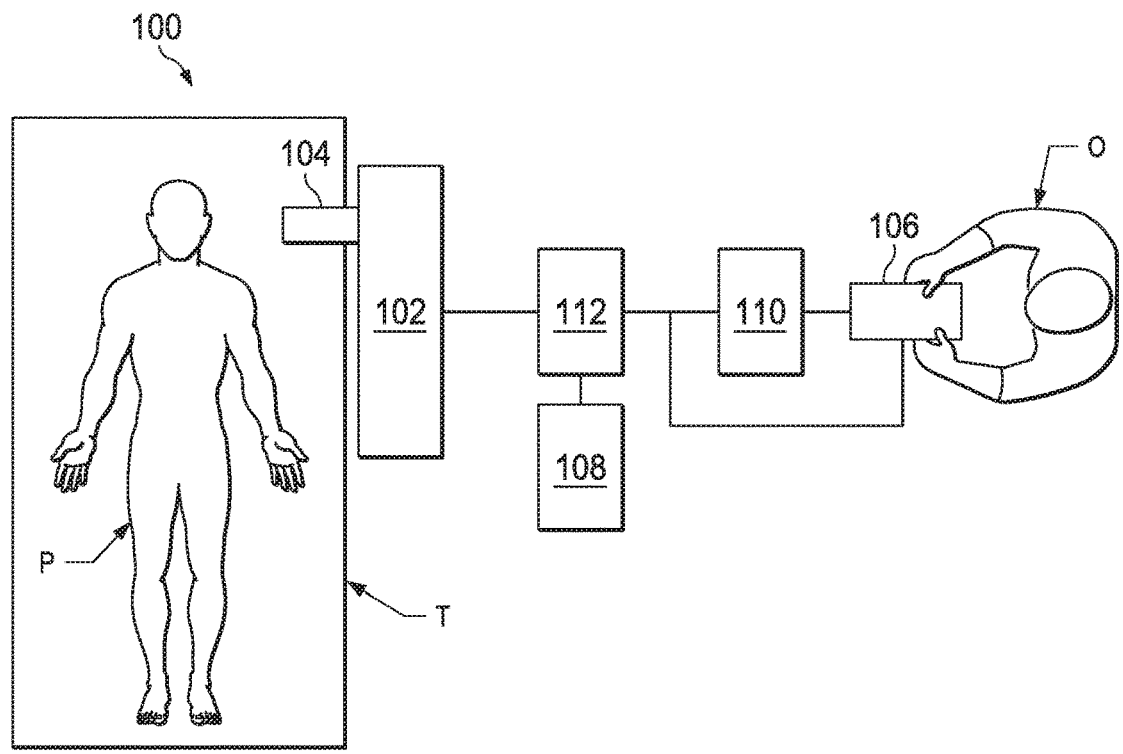
FIG. 1 is a simplified diagram of a teleoperated medical system according to some embodiments of the present disclosure.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. An operator input system 106 (sometimes called a master assembly 106) allows an operator a surgeon, a clinician, or a physician O as illustrated in FIG. 1) to view the interventional site and to control teleoperational manipulator assembly 102.

Master assembly 106 may be located at a physician's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, the teleoperated system 100 generally includes a teleoperational manipulator assembly 102 for operating a medical instrument 104 in performing various procedures on the patient P. The assembly 102 is mounted to or near an operating table O. A master assembly 106 allows an operator (e.g., a surgeon, a clinician, or a physician O as illustrated in FIG. 1) to view the interventional site and to control the teleoperational manipulator assembly 102.

The master assembly 106 (or master surgeon control inputs assembly 106) may be located at a surgeon's console which is usually located in the same room as operating table O. However, it should be understood that the physician O can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instruments 104 and still provide the physician O with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display system 110 and the operator input system 106 may be oriented so the physician O can control the medical instrument system 104 and the operator input system 106 with the perception of telepresence.

The display system 110 may also display an image of the surgical site and medical instruments captured by the visualization system. The display system 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display system 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments, often for purposes of imaged guided surgical procedures, the display system 110 may display a virtual navigational image in which the actual location of the medical instrument 104 is registered (i.e., dynamically referenced) with the preoperative or concurrent images/model to present the physician O with a virtual image of the internal surgical site from the viewpoint of the location of the tip of the instrument 104. In some examples, the viewpoint may be from a tip of medical instrument 104. An image of the tip of the instrument 104 or other graphical or alphanumeric indicators may be superimposed on the virtual image to assist the physician O controlling the medical instrument. Alternatively, the instrument 104 may not be visible in the virtual image.

In other embodiments, the display system 110 may display a virtual navigational image in which the actual location of the medical instrument is registered with preoperative or concurrent images to present the physician O with a virtual image of medical instrument within the surgical site from an external viewpoint. An image of a portion of the medical instrument or other graphical or alphanumeric indicators may be superimposed on the virtual image to assist the physician O controlling the instrument 104. As described herein, visual representations of data points may be rendered to the display system 110. For example, measured data points, moved data points, registered data points, and other data points described herein may be displayed on the display system 110 in a visual representation. The data points may be visually represented in a user interface by a plurality of points or dots on the display or as a rendered model, such as a mesh or wire model created based on the set of data points. In some embodiments, a visual representation may be refreshed in the display system 110 after each processing operations has been implemented to alter the data points.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a non-transitory machinereadable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, another portion of the processing being performed at master assembly 106, and the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

The control system 112 may further include a virtual visualization system to provide navigation assistance to physician O when controlling the medical instrument system(s) 104 during an image-guided surgical procedure. Virtual navigation using the virtual visualization system is based upon reference to the acquired preoperative or intra-operative dataset of the anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In some embodiments, the teleoperational system may include more than one teleoperational assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

The instrument system 200 includes an elongate device 202 (e.g., a catheter system) coupled to a drive unit 204. The elongate device 202 includes an elongated flexible body 216 having a proximal end 217 and a distal end 218 (or tip portion 218). In one embodiment, the flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may use any appropriate sensing technology or combination of sensing technologies, such as: OFDR (optical frequency domain reflectometry) techniques such as those using Fiber Bragg gratings, Raleigh scattering, or some other applicable reflection approach; position sensors enabled by EM (electromagnetic) techniques; linear rotary encoder techniques supported by capacitive, optical, resistive, or other technologies; etc. As a specific example, position sensor system 220 may comprise of, or be a component of, an EM sensor system with positional sensor system 220 including one or more conductive coils that may be subjected to an externally generated electromagnetic field. Each coil of such an EM sensor system used to implement position sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors used in some embodiments of position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instalment 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

When using a teleoperational assembly to insert a catheter (or other elongate, flexible medical instrument) into a patient anatomy, the catheter length external to the patient should be supported as it is advanced into the patient. Otherwise, as the catheter is pushed from a proximal end and encounters friction in the patient anatomy at the distal end, the catheter may buckle or bend. To prevent this deformation of the catheter, an instrument guiding apparatus may be used to provide support to the catheter at regular intervals as it enters the patient anatomy along an insertion axis. The catheter may be threaded into channels or eyelets of the instrument guiding apparatus before the catheter is introduced into the patient's anatomy. In the embodiments described herein, the instrument guiding apparatus can transition between a compressed configuration and an expanded configuration. In embodiments described herein, the guiding apparatus includes alignment elements that enable the eyelets of the guiding apparatus to self-align along the insertion axis before the catheter is introduced into the guiding apparatus. Generally, the catheter is introduced into the guiding apparatus while the apparatus is in a compressed configuration. After a distal portion of the catheter is threaded through the eyelets of the guiding apparatus, the guiding apparatus can be expanded about the remainder of the catheter. The instrument guiding apparatus returns to a compressed configuration as the catheter is advanced into the patient anatomy and the exposed length of the catheter decreases. As the catheter enters the patient anatomy, the guiding apparatus compresses and the alignment members guide the eyelets to realign with the insertion axis. In some embodiments, the instrument guiding apparatus described herein includes features that increase the rigidity and stability of the apparatus in an expanded configuration. Thus, the embodiments described herein effectively provide stable support to the catheter as it is introduced into, traverses through, and is removed from the patient anatomy.

Figure 3:
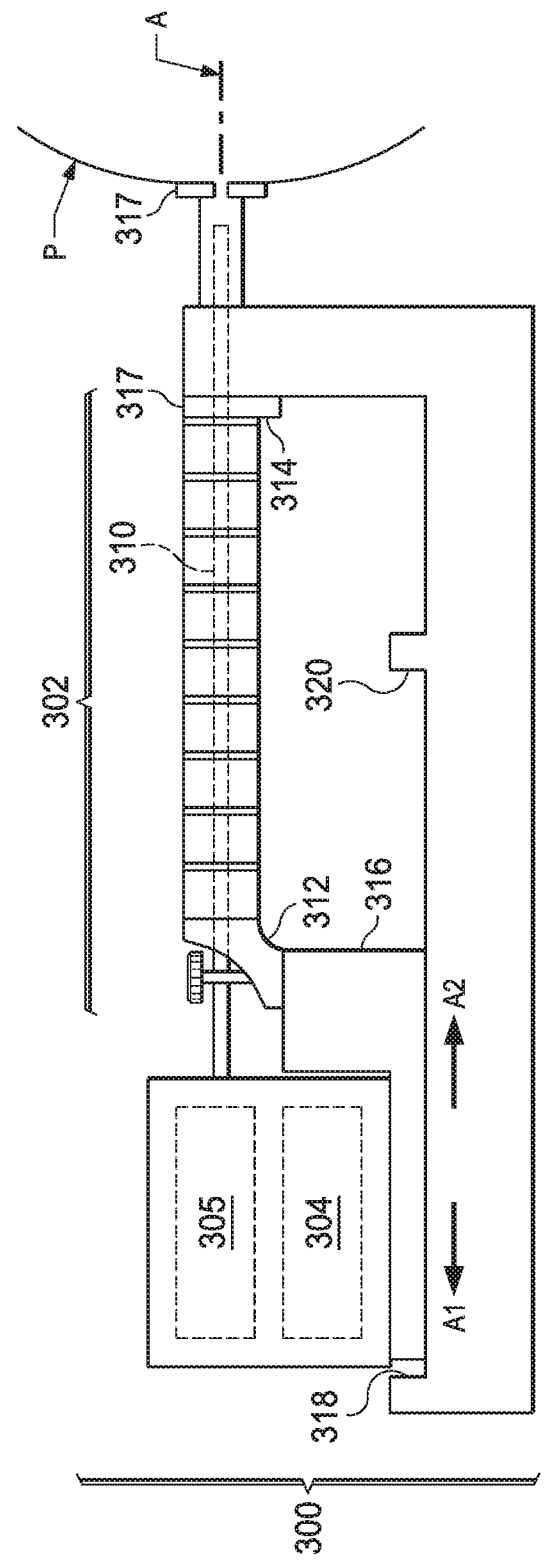
FIG. 3 is a simplified diagram of a side view of a teleoperational manipulator assembly, an elongate instrument, and an instrument guiding apparatus according to some embodiments of the present invention.

FIG. 3 diagrammatically illustrates an instrument interface portion 300 of a teleoperational manipulator assembly (e.g., teleoperational manipulator assembly 102) and an instrument guiding apparatus 302 according to an embodiment of the present invention. The instrument interface portion 300 includes drive inputs 304 that may provide mechanical coupling of the instrument end effector and flexible body steering mechanism to the drive motors mounted to the teleoperational manipulator. For example, a pair of drive inputs may control the pitch motion of the distal end of the instrument flexible body, with one adaptor of the pair controlling motion in the upward direction and the other of the pair controlling motion in the opposite downward direction. Other pairs of drive inputs may provide opposing motion in other degrees of freedom for the flexible body and/or the end effector. In some embodiments, the drive inputs 304 may be coupled to or positioned within an instrument control unit 305, which controls the positioning of an elongate instrument such as a catheter 310 Instrument interfacing with teleoperational or robotic manipulators is described, for example in U.S. Pat. No. 6,331,181, filed Oct. 15, 1999, disclosing "Surgical Robotic Tools, Data Architecture, And Use" and U.S. Pat. No. 6,491,701, filed Jan. 12, 2001 disclosing "Mechanical Actuator Interface System For Robotic Surgical Tools" which are both incorporated by reference herein in their entirety. The instrument interface portion 300 may also control instrument insertion by moving linearly along an insertion axis A.

During use, the catheter 310 is positioned within the instrument guiding apparatus 302 and the instrument guiding apparatus 302 acts to minimize the buckling of the catheter 310 as the catheter 310 advances toward, remains within, and retracts from the patient anatomy. The instrument guiding apparatus 302 has a proximal end 312 and a distal end 314. In some embodiments, the proximal end 312 of the instrument guiding apparatus 302 is detachably coupled to a mounting plate 316 of the instrument interface portion 300. The mounting plate 316 may be moveable (e.g., along the insertion axis A) relative to a proximal end 318 and a distal end 320 of the instrument interface portion 300. The proximal end 318 and the distal end 320 may or may not be disposed at the physical ends of the instrument interface portion 300. For example, in the pictured embodiment, the proximal end 318 and the distal end 320 comprise motion stops disposed away from the actual ends of the instrument interface portion 300 that are shaped and configured to halt the axial translation of the mounting plate 316. During use, the distal end 314 of the instrument guiding apparatus 302 may be detachably coupled to an anchor 317 within the surgical field. The anchor 317 may be positioned on the instrument interface portion 300 (e.g., on a flexible instrument manipulator or FIM), the surgical table, on a surgical frame, or on the patient anatomy. In one example, the anchor 317 may comprise a mouth guard clamped by patient's teeth. The instrument guiding apparatus 302 provides longitudinal support along the length of the catheter 310 positioned within the instrument guiding apparatus 302 to minimize buckling of the exposed length of the catheter 310 as it is pushed into the patient's body P.

Figure 5:
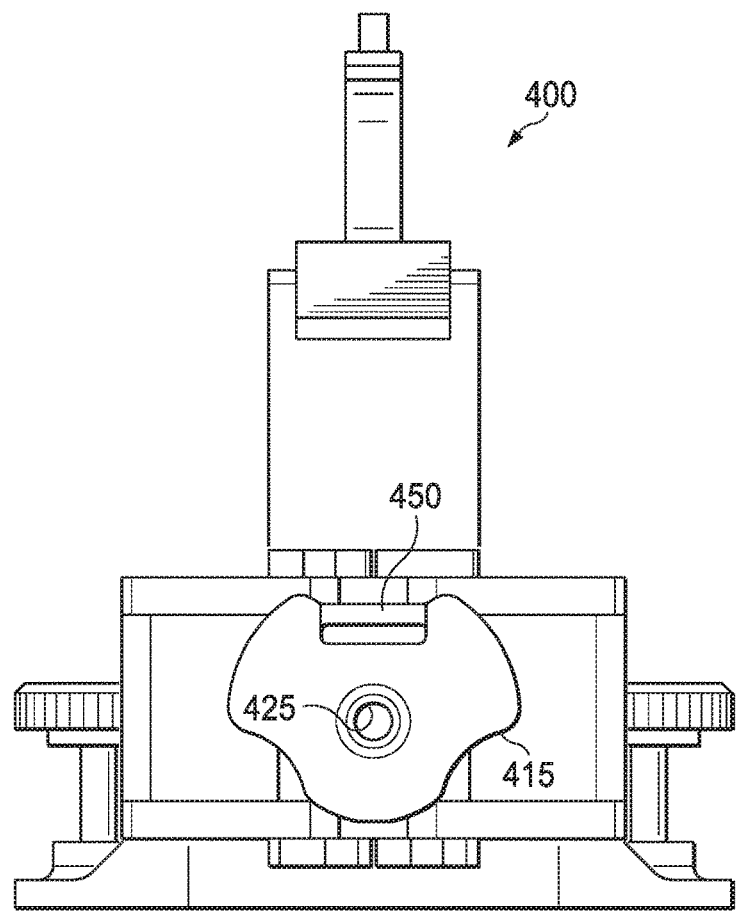
FIG. 5 illustrates a front view of the instrument guiding apparatus shown in FIG. 4.
Figure 4:
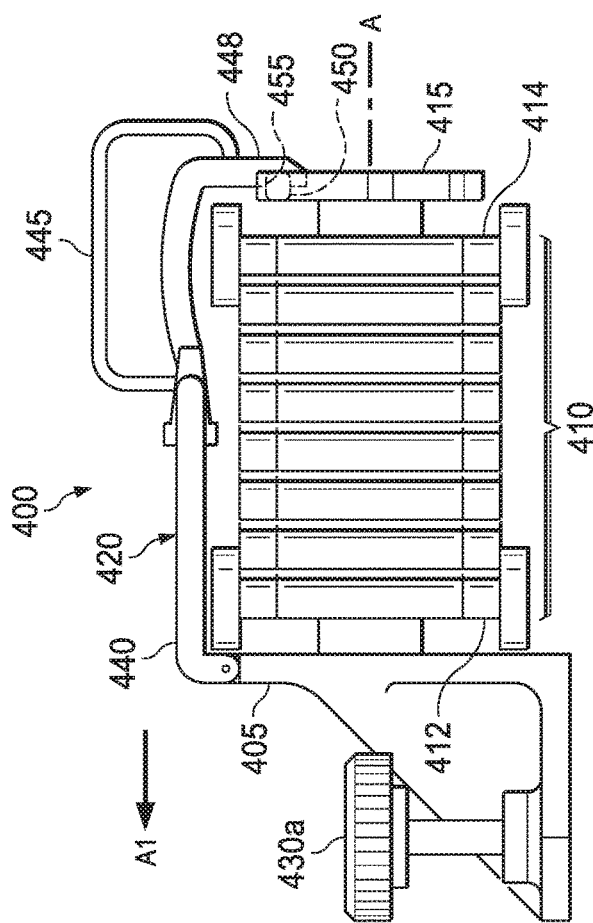
FIG. 4 illustrates a side view of the instrument guiding apparatus 400 in a compressed configuration.
Figure 6:
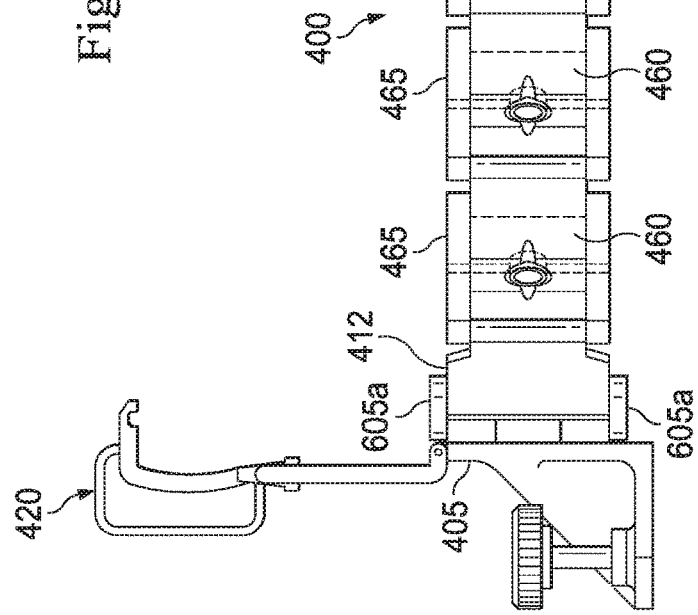
FIG. 6 illustrates a side view of the instrument guiding apparatus shown in FIG. 4 in an expanded configuration.

FIGS. 4-9 illustrate various views of an exemplary instrument guiding apparatus 400 according to one embodiment of the present disclosure. In particular, FIG. 4 illustrates a side view of the instrument guiding apparatus 400 in a compressed configuration. FIG. 5 illustrates a front view of the instrument guiding apparatus 400. FIG. 6 illustrates a side view of the instrument guiding apparatus 400 in an expanded configuration. FIG. 7 illustrates a top view of the instrument guiding apparatus 400 in an expanded configuration. FIG. 8 illustrates a bottom view of the instrument guiding apparatus 400 in an expanded configuration. FIG. 9 illustrates a perspective view of the instrument guiding apparatus 400 in an expanded configuration.

The instrument guiding apparatus 400 is a particular example of the instrument guiding apparatus 302 shown in FIG. 3. The design, function, and use of this specific embodiment are the same as described with reference to the instrument guiding apparatus 302 shown in FIG. 3 unless otherwise noted or apparent from the description. In the pictured embodiment, the instrument guiding apparatus 400 includes a proximal coupler 405, a variable-length support assembly 410 extending from a first end 412 to a distal end 414, a distal coupler 415 at the distal end 414, and a retaining assembly 420 such as a latch mechanism. In use, the catheter 310 may be threaded through a proximal aperture 422 (shown in FIG. 10A) on the proximal coupler 405, through the variable-length support assembly 410, and through a distal aperture 425 (shown in FIG. 5). The proximal aperture 422 may also be referred to as lumen 422. Initially, in some instances, the instrument guiding apparatus 400 can shift from the compressed configuration shown in FIG. 4 into the expanded configuration shown in FIGS. 6-9 after the catheter 310 is threaded distally through the variable-length support assembly 410. After the catheter 310 travels through the variable-length support assembly 410 and enters the patient, the instrument guiding apparatus 400 can shift from the expanded or extended configuration shown in FIGS. 6-9 to the compressed configuration shown in FIG. 4 into the as the catheter 310 is advanced distally into the patient along the insertion axis A. The instrument guiding apparatus 400 and the variable-length support assembly 410 extend as the catheter 310 is withdrawn from the patient and a longer length of catheter 310 is exposed outside the patient (i.e., the exposed of length of catheter 310 in need of support).

The proximal coupler 405 detachably couples the first end 412 of the variable-length support assembly 410 to the instrument interface portion 300 and/or the instrument control unit 305 via fastening elements 430a and 430b (shown in FIG. 7). In the pictured embodiment, the fastening elements 430a, 430b comprise shoulder screws or shoulder bolts that are shaped and sized to mate with corresponding threaded holes within the instrument interface portion 300 (e.g., on the mounting plate 316) and/or the instrument control unit 305 shown in FIG. 3. As shown in FIG. 8, the proximal coupler 405 includes threaded holes 435a, 435b, which are shaped and sized to receive the fastening elements 430a, 430b, respectively. After aligning the threaded holes 435a, 435b with the corresponding threaded holes in the instrument interface portion 300 and/or the instrument control unit 305, the fastening elements 430a, 430b may be inserted through the threaded holes 435a, 435b, respectively, and tightened to securely attach the instrument guiding apparatus 400 to the mounting plate 316 (or another part of the instrument interface portion 300 shown in FIG. 3). Other embodiments may include any of a variety of fastening elements capable of securely yet detachably coupling the proximal coupler 405 of the instrument guiding apparatus 400 to the teleoperational manipulator assembly, including, without limitation, snap-fit engagements, frictional engagements, hook-and-eye fasteners, pins, carriage bolts, and mating screws. The proximal coupler 405 includes a lumen 422 (shown in FIGS. 9 and 10A) that is sized and shaped to receive the catheter 310 (or other elongate member) into the instrument guiding apparatus 400. In some embodiments, the lumen 422 is linearly aligned with the distal aperture 425 in the distal coupler 415 along the insertion axis A.

As shown in FIG. 4, when the instrument guiding apparatus 400 is collapsed, the retaining assembly 420 may be used to selectively retain the variable-length support assembly 410 in the compressed configuration. In the pictured embodiment, the retaining assembly 420 comprises a hinged mechanism including a proximal section 440 and a distal section 445. The proximal section 440 is hingedly coupled to the proximal coupler 405 at one end and is hingedly coupled to the distal section 445 at the opposite end. The distal section 445 includes a distal fastener 448 shaped and sized to selectively engage an attachment element 450 disposed on the distal coupler 415. In the pictured embodiment, as shown in FIGS. 4 and 5, the distal fastener 448 is shaped as an indented hook sized to selectively latch onto the attachment element 450, which is shaped as a bar. In particular, the attachment element 450 is configured to snap into a corresponding indentation 455 on the distal fastener 448. In other embodiments, the distal fastener 448 and the attachment element 450 are shaped and sized as any of a variety of detachably mating fastening elements, including, without limitation, other snap-fit engagements, hook and eye fasteners, threaded engagements, and frictional engagements. In some instances, when the instrument guiding apparatus 400 is being transported or is being attached to the teleoperational manipulator assembly 102, or when the catheter 310 is being initially threaded through the instrument guiding apparatus 400, the retaining assembly 420 may be used to temporarily lock the variable-length support assembly 410 in the compressed configuration shown in FIG. 4. When the distal fastener 448 is detached from the attachment element 450, the distal section 445 can fold towards the proximal section 440, and both these sections 445, 440 can lift away from the variable-length support assembly 410 and fold in the direction of the arrow A1. After detaching the distal fastener 448 from the attachment element 450, the variable-length support assembly 410 is able to stretch into an expanded configuration, as shown in FIGS. 6-9.

In addition to cooperating with the retaining assembly 420 to retain the instrument guiding apparatus 400 in a compressed configuration, the distal coupler 415 may be used to detachably couple the instrument guiding apparatus 400 to the patient or another device (e.g., a stabilizer mounted to the patient or the surgical table) to stabilize the distal end of the instrument guiding apparatus as the catheter 310 is passed through the variable-length support assembly 410. For example, in some embodiments, the attachment element 450 of the distal coupler 415 may be connected to a stabilizer, such as, by way of non-limiting example, a hook or a tether, in the surgical field. During use, the stabilizer may be connected to the patient's body and/or the surgical table. In some instances, the stabilizer may comprise an introducer sheath at the insertion site configured to receive the catheter 310. The instrument guiding apparatus 400 provides support at discrete intervals along the length of the catheter 310 between the stabilizer and the proximal coupler 405. In general, the distal coupler 415 is stationary with respect to the patient.

The variable-length support assembly 410 can expand from the compressed configuration shown in FIG. 4 into the expanded configuration shown in FIGS. 6-9 as the proximal coupler 405 moves proximally in the direction of arrow A1 along the insertion axis A. In some instances, motion of the catheter 310 in and out of the patient anatomy is coupled to the motion of the proximal coupler 405. In some instances, the proximal coupler 405 moves in the direction of the arrow A2 in concert with the catheter 310 as the catheter 310 is initially advanced distally along the insertion axis A and into the patient anatomy. Similarly, in some instances, the proximal coupler 405 moves in the direction of the arrow A1 along the insertion axis A in concert with the catheter 310 as the catheter 310 is removed from the patient anatomy. The variable-length support assembly 410 may collapse or fold back into a compressed configuration as the instrument interface portion 300 and/or the instrument control unit 305 shown in FIG. 3 advances the catheter 310 further into the patient anatomy, thereby linearly displacing the variable-length support assembly 410 in the direction of arrow A2 along the axis A. When the catheter 310 is fully inserted into the patient, the variable-length support assembly 410 is in a compressed condition as illustrated in FIG. 4. When the catheter 310 is only partially inserted into the patient, the variable-length support assembly 410 is partially extended as shown in FIGS. 6-9. When the catheter 310 is fully withdrawn from the patient or at least retracted (e.g., into a delivery instrument) out of direct contact with patient anatomy, the variable-length support assembly 410 is fully extended.

As shown in FIG. 4, the variable-length support assembly 410 is disposed between the proximal coupler 405 and the distal coupler 415. As shown in FIGS. 6-9, the variable-length support assembly 410 includes multiple pairs of corresponding support members 460, 465 connected to each other to create an expandable scaffolding structure. The first support members 460 are coupled to the second support members 465 to create a support frame of pairs of support members 460, 465 assembled in an expandable scissor-like configuration. As shown in FIG. 7, when the instrument guiding apparatus 400 is in an expanded configuration, the first support members 460 interlace with the second support members 465 along a central axis CA to form the variable-length support assembly 410. The first support members 460 extend through and generally bisect the second support members 465 to form the crisscrossed, expandable variable-length support assembly 410.

FIGS. 10A-10D illustrate perspective views of a proximal portion of the variable-length support assembly 410 and the proximal coupler 405 according to one embodiment of the present disclosure. FIG. 10E illustrates a top view of a proximal portion of the variable-length support assembly 410 according to one embodiment of the present disclosure. FIG. 11A illustrates a perspective view of a central portion of the variable-length support assembly 410 according to one embodiment of the present disclosure. As shown by FIGS. 7, 8, and 11A, the variable-length support assembly 410 includes two proximal arms 470a, 470b, two distal arms 472a, 472b, and a repeating array of three main components: the first support member 460, the second support member 465, and an eyelet 475. FIG. 12 illustrates a perspective view of the first support member 460 and the eyelet 475 one embodiment of the present disclosure. FIG. 13 illustrates a perspective view of the second support member 465 one embodiment of the present disclosure. FIG. 14 illustrates a perspective view of the eyelet 475 according to one embodiment of the present disclosure.

As shown in FIG. 14, each eyelet 475 comprises a generally hollow cylinder or annular ring. In other embodiments, the eyelet 475 may comprise any of a variety of passageways with a variety of sizes and shapes. For example, some embodiments may include a rectangular or ovoid eyelet. The eyelets 475 are configured to receive pins or other securing elements in receiving holes 476a, 476b, which are positioned on opposite sides of an external surface 477 of the eyelet 475. In use, the eyelets 475 are configured to receive an elongate instrument, such as, without limitation, the catheter 310, a sheath, a guidewire, or any combination thereof. In the pictured embodiment, the eyelets 475 are sized and shaped to permit the easy passage of the catheter 310 therethrough. As shown in FIG. 14, the eyelet 475 includes a lumen 478 that has a diameter D1 that is sized to accommodate the catheter 310. The diameter D1 may range from 2 mm to 12 mm. In some embodiments, the diameter D1 measures 5 mm. Other diameters are contemplated. As shown in FIG. 12, the first support member 460 includes a central opening 480 that has a diameter D2 that is sized to accommodate a single eyelet 475. The diameter D2 may range from 4 mm to 24 mm. In some embodiments, the diameter D2 measures 10 mm. Other diameters are contemplated. The eyelet 475 has a thickness T1, and the central opening 480 of the first support member 460 has a central thickness T2 and an outer thickness T3. In the pictured embodiment, the thickness T1 of the eyelet 475 is approximately the same as the central thickness T2. In other embodiments, the thickness T1 may be greater than or less than the central thickness T2. The thickness T1 may range from 2 mm to 18 mm. In some embodiments, the thickness T1 measures 6 mm. The central thickness T2 may range from 2 mm to 12 mm. In some embodiments, the central thickness T2 measures 5 mm. The outer thickness T3 may range from 2 mm to 12 mm. In some embodiments, the outer thickness T3 measures 5 mm. Other thicknesses are contemplated.

In the pictured embodiment, both the first support members 460 and the second support members 465 have a generally rectangular profile. Other shapes, however, are contemplated for the support members, including without limitation, square, oblong, rhomboid, and elliptical shapes. In particular, the first support member 460 is shaped as a rectangular plate having the central opening 480. The first support member 460 includes two indentations 484a, 484b that flank the central opening 480 of the first support member 460. As shown in FIG. 12, the first support member 460 includes a height H1. The height H1 may range from 6 mm to 54 mm. In some embodiments, the height H1 measures 18 mm. Other heights are contemplated. Other heights are contemplated. As shown in FIG. 13, the second support member 465 comprises an upper bar 481, a lower bar 482, and two walls 483a, 483b. The walls 483a, 483b have an outer thickness T4. In the pictured embodiment, the outer thickness T4 is approximately the same as the outer thickness T3 of the first support member 460. In other embodiments, the thickness T4 may be greater than or less than the thickness T3. The outer thickness T4 may range from 2 mm to 12 mm. In some embodiments, the outer thickness T4 measures 18 mm. Other thicknesses are contemplated. The walls 483a, 483b of the second support member 465 include notches 486a, 486b, respectively. In the pictured embodiment, the notches 486a, 486b comprise hemi-elliptical cutouts in the walls 483a, 483b. As shown in FIG. 13, the space between the upper bar 481 and the lower bar 482 of the second support member 465 includes a height H2. The height H2 may range from 6 mm to 54 mm. In some embodiments, the height H2 measures 18 mm. Other heights are contemplated. The second support member 465 includes a height H3. The height H3 may range from 10 mm to 80 mm. In some embodiments, the height H3 measures 30 mm. Other heights are contemplated.

Figure 10A:
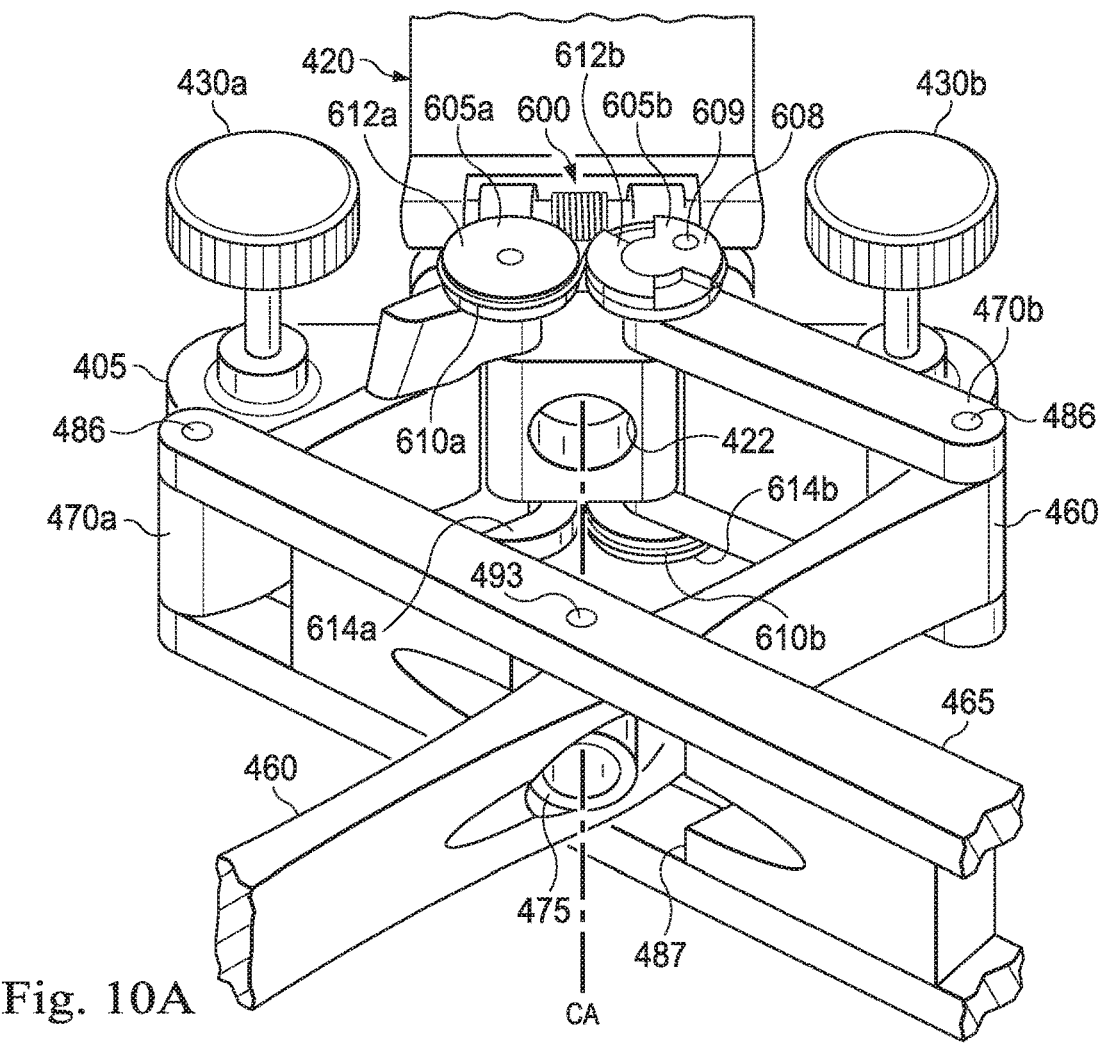
FIGS. 10A-10E illustrate a proximal portion of the variable-length support assembly shown in FIG. 4. In particular.
Figure 10D:
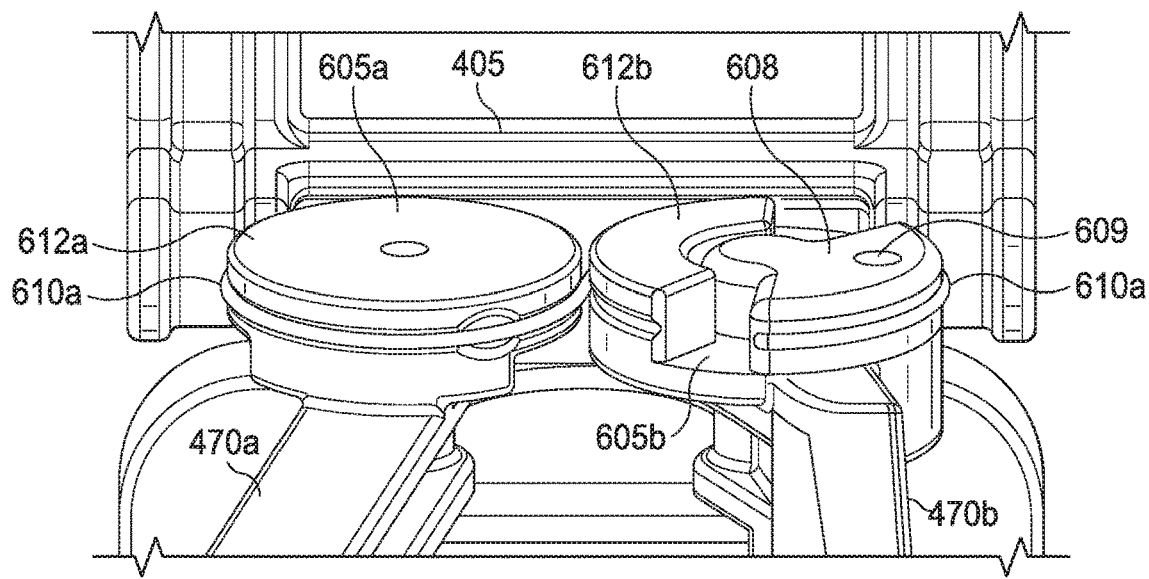

As shown in FIGS. 10A and 11A, each first support member 460 intersects the corresponding second support member 465 by extending through a central window 487 of the second support member 465. The first support member 460 is coupled to the intersecting second support member 465 at a central hinge 493 aligned with a vertical axis VA that bisects the centroid of the eyelet 475. As shown in FIGS. 12 and 13, the central hinge comprises first and second pins 485a, 485b, which are inserted through the first and second support members 460, 465, respectively, into the top and bottom parts, respectively, of the eyelet 475 along the vertical axis VA. The eyelet 475 is movably or rotatably coupled to the first support member 460 and the second support member 465 at the central hinge 493 by first and second pins 485a, 485b. In the pictured embodiment, the central hinge 493 comprises a pin joint with the first and second pins 485a, 485b extending through channels in the first and second support members 460, 465 into the receiving holes 476a, 476b in the eyelet 475. For example, in the pictured embodiment, the first pin 485a extends through the channels 490a, 490b in the first and second support members 460, 465, respectively, and the second pin 485b extends through channels 495a, 495b in the first and second support members 460, 465, respectively. Thus, the eyelet 475 is coupled to both the first and second support members 460, 465 by the first and second pins 485a, 485b, and can pivot 360 degrees about the vertical axis VA within the central opening 480 of the first support member 460.

Returning to FIGS. 10A, 10B, and 11A, adjacent support members 460, 465 are hingedly coupled to each other at their ends at outer hinges 486. In some embodiments, as shown in FIG. 11, the outer hinges 486 comprise pin joints with pins, bolts, or screws extending through peripheral attachment holes 498, 499 in the first support member 460 and the second support member 465, respectively. In other embodiments, as shown in FIGS. 11B-11D, the outer hinges may comprise living hinges or thin flexible hinges that are continuations of the support members themselves. FIGS. 11B-11D illustrate perspective views of a central portion of an exemplary variable-length support assembly according to another embodiment of the present disclosure. FIG. 11B illustrates a close-up perspective view of exemplary support members linked by living hinges in an expanded configuration according to one embodiment of the present disclosure. FIG. 11C illustrates a perspective view of the variable-length support assembly in an expanded configuration according to one embodiment of the present disclosure. FIG. 11D illustrates a perspective view of the variable-length support assembly in a compressed configuration according to one embodiment of the present disclosure.

In particular, FIGS. 11B-11D illustrate an exemplary variable-length support assembly 410' including outer hinges 486' that comprise living hinges or thin flexible hinges made from the same material as the two support members 460', 465'. The variable-length support assembly 410' is substantially similar to the variable-length support assembly 410 except for the living hinges described herein. For example, the outer hinges 486' may be made of partially oriented polypropylene, polyethylene, or ultra-high molecular weight polyethylene. In such embodiments, the outer hinges 486' may be sections of wall connecting the support members 460', 465' that are thinner than the outer thickness T3 of the first support member 460' and the outer thickness T4 of the second support member 465' (as suggested in FIGS. 12 and 13), thereby allowing for flexing along the line of the outer hinge 486' with adequate range of bending and kinematic constraint. In the pictured embodiment, the outer hinges 486' have an arcuate or semi-circular cross-sectional profile when the variable-length support assembly 410' is in an expanded condition. Such living hinges have minimal friction and low wear, and the low cost and ease of manufacturing can be advantageous. In other embodiments, the support members 460, 465 may be manufactured as mating halves so that the interlaced opposing support members can be assembled from multiple identical pairs of molded parts or two complementary molded parts. For example, in some embodiments, the support members 460', 465' may be manufactured as mating pairs of first and second support members 460', 465' linked at central hinges 493'. In other embodiments, the support members 460', 465' may be manufactured as two separate chains of the first support members 460' and the second support members 465' linked at the outer hinges 486'.

Returning to FIG. 4, when the variable-length support assembly 410 is collapsed in a compressed configuration, the support members 460, 465 are positioned adjacent one another. In contrast, as shown in FIGS. 6-11A, when the variable-length support assembly 410 is spread out in an expanded configuration, the support members 460, 465 are spaced apart from each other in a scissor-like configuration. More specifically, the support members 460, 465 pivot relative to each other at the central hinges 493 and the outer hinges 486, thereby forcing the eyelets 475 to separate from one another at regular intervals.

In the pictured embodiment described above with respect to FIGS. 10A and 11A in particular, the eyelets 475 align along the insertion axis A as the catheter 310 passes through them (e.g., when the catheter 310 passes through the instrument guiding apparatus 400 in the compressed configuration shown in FIG. 4). However, in this embodiment, all the eyelets 475 may not be aligned when the variable-length support assembly 410 is returned to a compressed configuration (e.g., without the catheter 310 passing through the eyelets 475 and maintaining their alignment). For example, one or more eyelets 475 may be turned along the vertical axis VA such that the catheter may encounter resistance as it is subsequently advanced into the variable-length support assembly 410. In such embodiments, a user may need to manually realign individual eyelets 475 or maneuver the catheter 310 to nudge the eyelets 475 into proper alignment before advancing the catheter 310.

In other embodiments, the instrument guiding apparatus 400 includes alignment members that ensure that the eyelets 475 are automatically aligned to form a pathway for the catheter 310 without needing to manually readjust individual eyelets 475. For example, FIGS. 15-18B describe two embodiments of variable length support assemblies that include different types of alignment members that facilitate eyelet self-alignment.

FIG. 15 illustrates portions of a variable-length support assembly 500 which can be included in instrument guiding apparatus 400. In particular, FIG. 15 illustrates an exemplary eyelet 505 having alignment members 510a, 510b extending laterally from an outer wall 515. The eyelet 505 is substantially similar to the eyelet 475 described above with reference to FIG. 14 except for the differences described herein. The eyelet 505 is configured to receive pins 485a, 485b in receiving holes 506a, 506b, respectively, which are positioned on opposite sides of the eyelet 505. Each alignment member 510a, 510b comprises an elongate bar 520a, 520b, respectively, which may have a round, rectangular or other prismatic or tapered shape, that optionally also may terminate in a protrusion 525a, 525b. In the pictured embodiment, the protrusions 525a, 525b are shaped as spheres, but other embodiments may have differently shaped protrusions, such as, without limitation, cubes, tabs, or cones. In other embodiments, the alignment members 510a, 510b may lack the protrusions 525a, 525b entirely. The alignment members 510a, 510b are fixed to opposite sides of the eyelet 505 in a horizontal orientation (i.e., on a horizontal axis HA perpendicular to the vertical axis VA).

FIGS. 16A-16B illustrate portions of a variable-length support assembly 501 which can be included in instrument guiding apparatus 400. FIGS. 16A and 16B illustrate top views of a first support member 530, a second support member 535, the eyelet 505, and the alignment members 510a, 510b. The first and second support members 530, 535 are substantially similar to the first and second support members 460, 465, respectively, described above except for the differences described herein. FIG. 16A illustrates a top view of the first and second support members 530, 535 in an expanded configuration, whereas FIG. 16B illustrates a top view of the first and second support members 530, 535 in a compressed configuration. The first support member 530 includes a first indentation 540a and a first groove 541a on a first wall 545 and a second indentation 540b and a second groove 541b on a second wall 550. The inner wall comprising the first wall 545 is on an opposite side of the first support member 530 than the second wall 550. The second support member 535 includes a third indentation 555a and a third groove 556a on a first wall 560 and a second indentation 555b and a fourth groove 556b on a second wall 565. The inner wall comprising the first wall 560 is on an opposite side of the second support member 535 than the second wall 565. The grooves 541a,b and 556a,b are shaped and sized to complement the shape of the elongate bar 520a, 520b, respectively. The indentations 540a, 540b, 555a, and 555b are shaped and sized to complement the shape of the protrusions 525a, 525b. For example, in the pictured embodiment, the indentations 540a, 540b, 555a, and 555b have a hemi-spherical shape corresponding to the spherical shape of the protrusions 525a, 525b. In other embodiments, the indentations 540a, 540b, 555a, and 555b may have a conical shape to help guide the protrusions 525a, 525b into mating positions. When the variable-length support assembly 501 is in a compressed configuration, the first and second support members 530, 535 pivot above the central hinge 493 such that the protrusions 525a, 525b can be interposed between the first support member 530 and the second support members 535. In particular, the protrusion 525a is positioned within the indentations 540a and 555a of the first support member 530 and second support member 535, respectively. The protrusion 525b is positioned within the indentations 540b and 555b of the first support member 530 and second support member 535, respectively. In some embodiments, the walls of the first support member 530 and the second support member 535 include grooves or elongate indentations (not shown) designed to receive the elongate bars 520a, 520b interposed therebetween. When the alignment elongate bars 520a, 520b are interposed between the walls of the support members 530 and 535 within grooves or elongate indentations in the walls of support members 530 and 535 or when the protrusions 525a, 525b are secured within the indentations 540a, 540b, 555a, and 555b, the eyelet 505 is forced into alignment with the other eyelets in the variable-length support assembly (i.e., with the insertion axis A shown in FIG. 4).

FIGS. 17-18B illustrate portions of an exemplary variable-length support assembly 690 which can be included in instrument guiding apparatus 400. In particular, FIG. 17 illustrates an exemplary eyelet 605 having alignment members 611a, 611b extending laterally from an outer wall 615. The eyelet 605 is substantially similar to the eyelet 475 described above except for the differences described herein. FIGS. 18A and 18B illustrate top views of a first support member 630, a second support member 635, the eyelet 605, and the alignment members 611a, 611b. The first and second support members 630, 635 are substantially similar to the first and second support members 460, 465, respectively, described above except for the differences described herein. FIG. 18A illustrates a top view of the first and second support members 630, 635 in an expanded configuration, whereas FIG. 18B illustrates a top view of the first and second support members 630, 635 in a partially compressed configuration. The alignment members 611a, 611b are fixed to opposite sides of the eyelet 605 in a horizontal orientation (i.e., on a horizontal axis HA perpendicular to the vertical axis VA). Each alignment member 611a, 611b comprises an elongate bar 620a, 620b, respectively, that extends from the eyelet 605 and telescopically couples with additional linkages that connect the elongate bars 620a, 620b to the support members 630, 635. In particular, the first elongate bar 620a couples to a first forked linkage 625a, and the second elongate bar 620b couples to a second forked linkage 625b. The forked linkages 625a, 625b are three-pronged linkages. The first forked linkage 625a includes three links that each connect to the elongate bar 620a: a central link 626a telescoping over the elongate bar 620a, a first peripheral link 627a connecting the central link 626a and the elongate bar 620a to the first support member 630, and a second peripheral link 628a connecting the central link 626a and the elongate bar 620a to the second support member 635. The second forked linkage 625b includes three links that each connect to the elongate bar 620b: a central link 626b telescoping over the elongate bar 620b, a first peripheral link 627b connecting the central link 626b and the elongate bar 620b to the first support member 630, and a second peripheral link 628b connecting the central link 626b and the elongate bar 620b to the second support member 635. Other embodiments may have differently shaped linkages shaped and configured to hingedly connect the elongate bars 620a, 620b with the support members 630, 635 such that the eyelets 605 are self-aligning when creating a passageway for the catheter 310.

When the instrument guiding apparatus 400 transitions to a compressed configuration, as shown in FIG. 18B, the first and second support members 630, 635 pivot above the central hinge 493 such that the forked linkages 625a, 625b can be interposed therebetween. In particular, the first forked linkage 625a and the second forked linkage 625b slide apart in a telescoping manner from the elongate bars 620a, 620b, respectively, thereby lengthening the alignment members 611a, 611b and allowing the linkages 625a, 625b to fold flat between the support members 630, 635. In this embodiment, the alignment members 611a, 611b continuously guide the eyelet 605 into constant alignment with the insertion axis A shown in FIG. 4, and consequently, all the other eyelets in the variable-length support assembly that possess similar alignment members. In some embodiments, the linkages 625a, 625b comprise living hinges and function as pivots rather than conventional linkages.

In another embodiment, as shown in FIGS. 19A-20D, the alignment members may comprise torsion springs. FIGS. 19A-19C illustrate an exemplary eyelet 705 having alignment members 710a, 710b extending from an outer wall 715. The eyelet 705 is substantially similar to the eyelet 475 described above except for the differences pictured and described herein. In particular, the alignment members 710a, 710b comprise torsion springs extending from attachment features 722a, 722b, respectively. The torsion springs comprising the alignment members 710a, 710b include coil portions 724a, 724b, prong portions 726a, 726b, and tail portions 728a, 728b respectively. The coil portions 724a, 724b of the torsion springs comprising the alignment members 710a, 710b wind around the attachment features 722a, 722b, respectively. The prong portions 726a, 726b and the tail portions 728a, 728b are continuous extensions from either end of the coil portions 724a, 724b of the alignment members 710a, 710b, respectively. The tail portions 728a, 728b are anchored within the eyelets 705.

FIGS. 20A-20D illustrate perspective views of an exemplary variable-length support assembly 720 including the eyelet 705 according to one embodiment of the present disclosure. As shown in FIGS. 20A-20D, the alignment members 710a, 710b are shaped and configured to apply equal forces between the eyelet 705 and first and second support members 730, 735 located on opposite sides of the eyelet 705 as the variable-length support assembly 720 extends and compresses. The prong portions 726a, 726b are sized and shaped to interact with the first support member 730 and second support member 735 of the variable-length support assembly 720. In the pictured embodiment, the prong portions 726a, 726b comprise substantially straight, elongate rods that are shaped and sized to apply a biasing force against the first and second support members 730, 735 to maintain the eyelet 705 in alignment with the other eyelets 705 along the central axis CA extending through the variable-length support assembly 720.

In yet another embodiment, as shown in FIGS. 21 and 22A-22C, the alignment members may comprise spring flexures. FIG. 21 illustrates an exemplary eyelet 805 having alignment members 810a, 810b extending from an outer wall 815. The eyelet 805 is substantially similar to the eyelet 475 described above except for the differences described herein. In the pictured embodiment, the alignment members 810a, 810b comprise spring flexures extending laterally from opposite sides of the eyelet 805.

FIGS. 22A-22C illustrate perspective views of an exemplary variable-length support assembly 820 including the eyelet 805 according to one embodiment of the present disclosure. The alignment members 810a, 801b are shaped, sized, and positioned to bear on the faces of first and second support members 830, 835 continuously over the full range of opening and closing between them as the variable-length support assembly 820 extends and compresses. As shown in FIGS. 22A-22C, the alignment members 810a, 810b are shaped and configured to apply biasing force against the first and second support members 830, 835, respectively, located on opposite sides of the eyelet 805 as the variable-length support assembly 820 extends and compresses. Distal tips 826a, 826b of the alignment members 810a, 810b, respectively, are sized and shaped to interact with the first support member 830 and second support member 835, respectively, of the variable-length support assembly 820. In the pictured embodiment, the alignment members 810a, 810b comprise curved, elongate bars or arms that are shaped and sized to apply a biasing force against the first and second support members 830, 835 to maintain the eyelet 805 in alignment with the other eyelets 805 along the central axis CA extending through the variable-length support assembly 820.

In another embodiment, as shown in FIGS. 23 and 24A-24C, the alignment members may comprise magnets. While magnets can provide for alignment of eyelets along the insertion axis, the magnets may also be used to retain variable length support assembly 920 in a compressed configuration for stowage, replacing or supplementing a latch mechanism such as retaining assembly 420 FIG. 23 illustrates an exemplary eyelet 905 having alignment members 910a, 910b coupled to an outer wall 915. The eyelet 905 is substantially similar to the eyelet 475 described above except for the differences described herein. In the pictured embodiment, the alignment members 910a, 910b comprise magnets having pole axes aligned with a longitudinal axis LA of a lumen 925 in each eyelet 905. In the pictured embodiment, the alignment members 910a, 910b comprise cylindrical magnets that are seated within the outer wall 915. The alignment members 910a, 910b are positioned approximately 180 degrees apart from one another and aligned along a horizontal axis HA, which extends through the center of the lumen 925. In other embodiments, the magnetic alignment members 910a, 910b may be positioned in different arrangements relative to the lumen and to each other. For example, magnets can comprise rings which are concentrically seated around lumen 920. Eyelet 905 can include a first ring magnet seated on a distal surface of eyelet 905 and a second ring magnet seated on a proximal surface of eyelet 905 allowing adjacent eyelets 905 within variable-length support assembly 920, to mate and magnetically attract when the variable-length support assembly is in the compressed configuration.

FIGS. 24A-24C illustrate perspective views of an exemplary variable-length support assembly 920 including the eyelet 905 according to one embodiment of the present disclosure. The alignment members 910a, 901b are shaped, sized, and positioned to maintain the eyelets 905 in alignment along the central axis CA extending through the lumens 925 continuously over the full range of extension and compression of the variable-length support assembly 920. As shown in FIGS. 24A-24C, the alignment members 910a, 910b are arranged such that magnetic attraction between the alignment members of adjacent eyelets 905 maintains the alignment of the eyelets 905 as the variable-length support assembly 920 extends and compresses. In the pictured embodiment, the magnetic attraction between the alignment members 910a, 910b of adjacent eyelets 905 to maintain the adjacent eyelets 905 in alignment with each other and, consequently, with the other eyelets 905 arranged in series along the central axis CA, which extends through the variable-length support assembly 920.

The alignment members 910a, 910b on opposite sides of the eyelets 905 may be positioned within the eyelets 905 to have opposite polarities. In other words, the alignment members 910a of adjacent eyelets 905 may have opposite polarities, and the alignment members 910b of adjacent eyelets 905 may have opposite polarities. Thus, the facing walls of adjacent eyelets 905 in the variable-length support assembly 920 may have opposite polarities causing the eyelets 905 to align. In particular, the alternating polarities will force the eyelets to align along the central axis CA (and the insertion axis A) as the variable-length support assembly 920 retracts toward the fully closed configuration. This ensures that whenever the variable-length support assembly 920 is retracted without a flexible instrument inserted through the eyelets 905, the eyelets 905 will align themselves as the variable-length support assembly 920 reaches its fully retracted configuration, thus preventing a misaligned eyelet 905 from interfering with full retraction of the variable-length support assembly 920. Such magnetic alignment members 910a, 910b may also eliminate the need for a mechanical latch (such as the retaining assembly 420 described above) to hold the assembly 920 closed when not attached at both ends to the flexible instrument manipulator system (i.e., the instrument interface portion 300).

As described above, the variable-length support assemblies can support the catheter 310 shown in FIG. 3 along its changing external (i.e., positioned outside the patient anatomy P) length as it enters or exits the patient anatomy P (shown in FIG. 1). When the variable-length support assembly is in a compressed configuration, the alignment members force the eyelets to self-align along a common axis (e.g., the insertion axis). When the catheter 310 is threaded through the support assembly, the catheter 310 is automatically aligned along the insertion axis and is protected from buckling by being supported at regular intervals at each eyelet. With the support members in an expanded configuration, the support assembly minimizes bending or buckling of the catheter 310 as the distal end of the catheter is advanced into the patient anatomy P. Any significant bending or buckling of the catheter 502 may damage optical fibers used for shape sensing or endoscopy or damage the catheter itself. Also, bending or buckling may make advancing the catheter non-intuitive, since the user will observe no distal tip movement even though the user is advancing the proximal end of the catheter.

FIGS. 10A-10E illustrate a proximal portion of the variable-length support assembly shown in FIG. 4. In particular, FIGS. 10A-10D illustrate perspective views of an exemplary proximal arm synchronizing assembly 600, and FIG. 10E illustrates a top view of the proximal arm synchronizing assembly 600 according to one embodiment of the present disclosure. The proximal arm synchronizing assembly 600 is connected to the proximal coupler 405, and serves to constrain the motion of the variable-length support assembly 410. In particular, the proximal arm synchronizing assembly 600 ensures that the variable-length support assembly 410 extends and retracts in alignment with the central axis CA (shown in FIGS. 7-9) extending through the proximal coupler 405 and the eyelets 475.

Figure 10B:
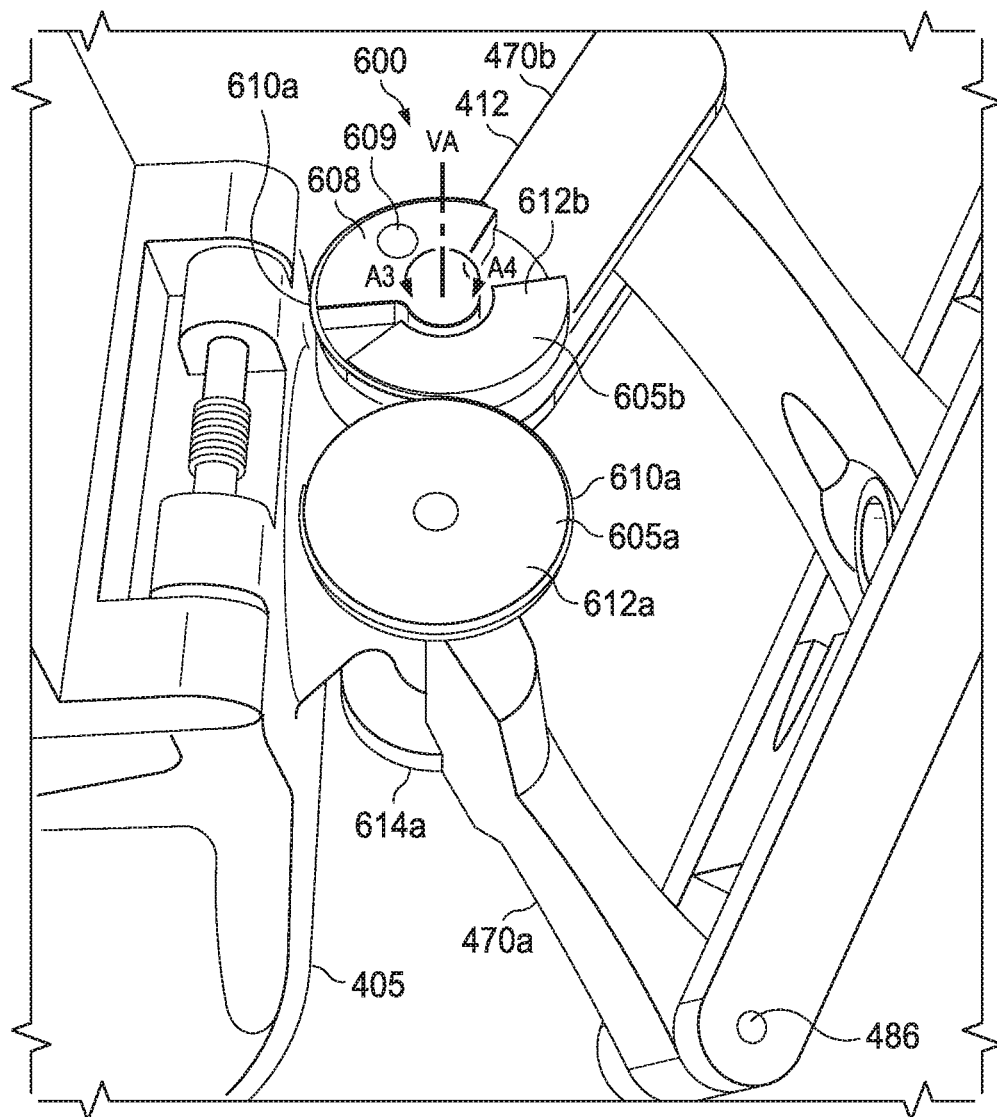
Figure 10C:
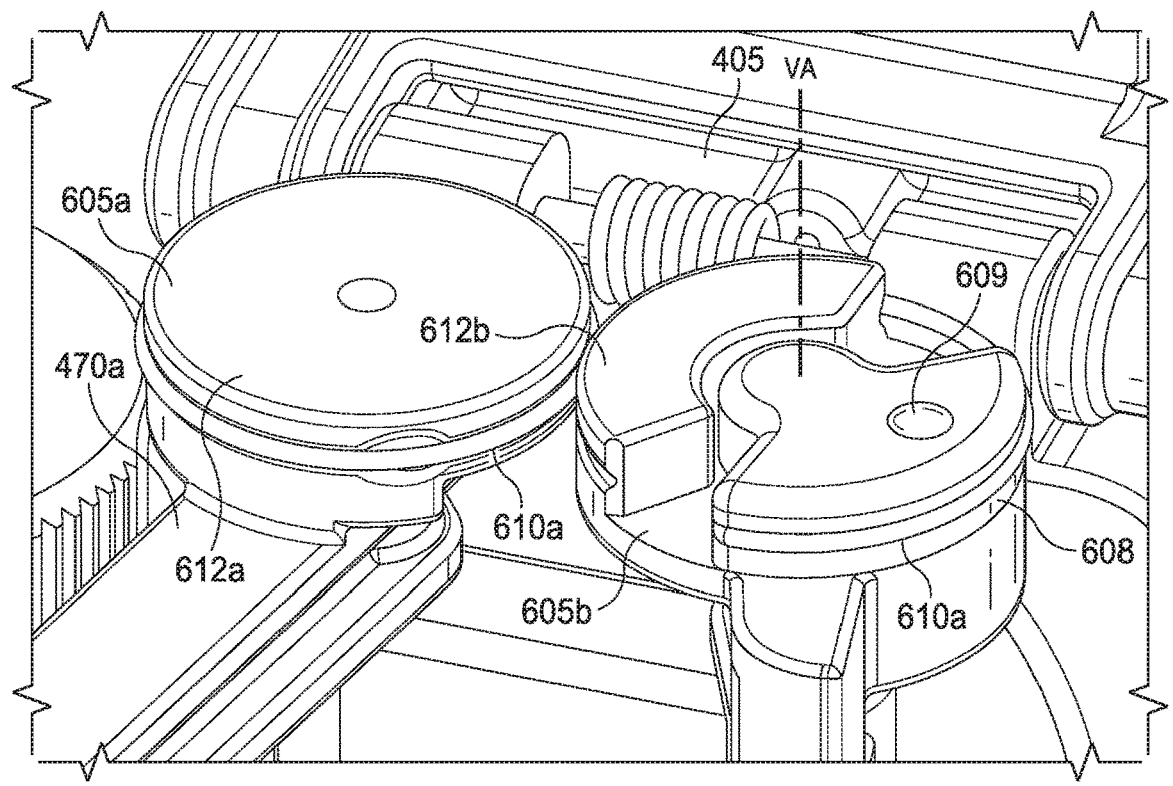
Figure 10E:
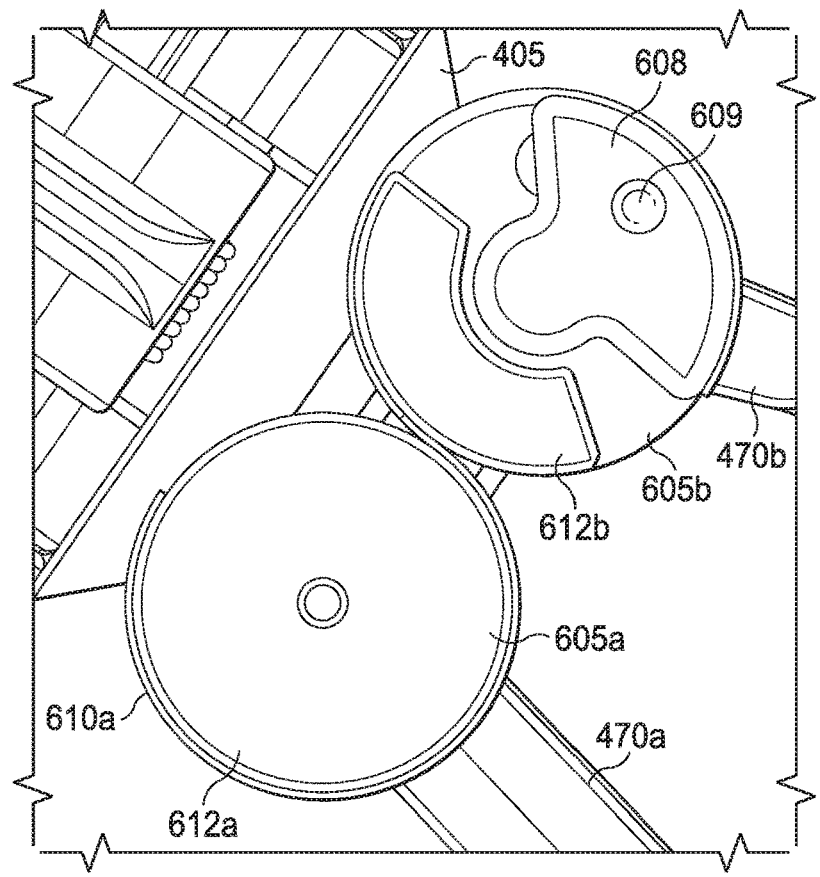

In the pictured embodiment, the proximal arm synchronizing assembly 600 comprises at least two spools 605a and 605b. The spools 605a, 605b are coupled to the proximal arms 470a, 470b, respectively. In some embodiments, the spools 605a, 605b are integral features of the proximal arms 470a, 470b, respectively. Each spool 605a, 605b may comprise two separate spools (i.e., an upper spool and a lower spool) that are independently coupled to the upper and lower cables 610a, 610b, respectively. For the sake of simplicity, each set of upper and lower spools is referred to herein as two single spools 605a, 605b. It is understood that the upper and lower spools may operate independently of one another, and may wind in opposing directions to synchronize the motion of the proximal arms 470a, 470b and the support members 460, 465. The cables 610a, 610b are wound around the spools 605a, 605b in opposing S-shapes to (1) synchronize the proximal arms 470a, 470b, (2) to equally actuate the first and second support members 460, 465 of the variable-length support assembly 410 relative to one another, and (3) to stabilize and steady the connection between the proximal coupler 405 and the variable-length support assembly 410 to prevent sagging of the variable-length support assembly 410 if the attachment of distal coupler 415 to an anchor such as anchor 317 of FIG. 3, is released by a user while a catheter is threaded through the variable-length support assembly 410. In particular, the cable 610a is wound about upper portions 612a, 612b of the spools 605a, 605b, respectively, and the cable 610b is wound about lower portions 614b, 614b of the spools 605a, 605b, respectively. The spool 605b includes at least one tensioning element 608 that is coupled to one end of the cable 610a. In the pictured embodiment, as shown in FIG. 10B, the tensioning element 608 is rotatable in the directions indicated by arrows A3, A4 about a vertical axis VA extending through the center of the spool 605b. Rotation of the tensioning element 608 acts to increase or decrease the tension in the cable 610a. For example, in the pictured example, rotation of the tensioning element 608 in the direction of the arrow A3 acts to decrease the tension on the cable 610a and rotation of the tensioning element 608 in the direction of the arrow A4 (i.e., the opposite direction) acts to increase the tension on the cable 610a. The tensioning element 608 includes an engagement feature 609 that facilitates the rotation of the tensioning element 608. In the pictured embodiment, the engagement feature 609 is an indentation on the tensioning element 608. The engagement feature 609 can selectively couple with a tool configured to rotate or otherwise adjust the tensioning element 608.

Because the upper and lower cables 610a, 610b are wound in opposite directions, the tensions in these cables 610a, 610b prevent unequal motion of the proximal arms 470a, 470b in respective opposite directions, thereby ensuring that the proximal arms 470a, 470b always open and close while maintaining equal but opposite angles with respect to the center axis CA of the variable-length support assembly 410. Increasing the tension on the cable 610a serves to increasingly constrain the motion of the support members. Thus, the cables 610a, 610b of the proximal arm synchronizing assembly 600 effectively constrain the support members 460, 465 of the variable-length support assembly 410 to move along the center axis CA.

In other embodiments, as shown in FIGS. 25A-25C, sets of gears with equal numbers of teeth may be substituted for the spools 605a, 605b and provide the same constraint on motion of the proximal arms 470a, 470b. In particular, FIGS. 25A-25C illustrate perspective views of an exemplary variable-length support assembly 950 coupled to a proximal arm synchronizing assembly 955 and a distal arm synchronizing assembly 960 according to one embodiment of the present disclosure. FIG. 25A illustrates the length of the variable-length support assembly 950. FIG. 25B illustrates the proximal arm synchronizing assembly 955 coupled to the variable-length support assembly 950, and FIG. 25C illustrates the distal arm synchronizing assembly 960 according to one embodiment of the present disclosure. In the pictured embodiment, the variable-length support assembly 950 includes a plurality of first support members 962 coupled to second support members 964. The proximal arm synchronizing assembly 955 is connected to the proximal coupler 405, and serves to constrain the motion of the variable-length support assembly 950. In particular, the proximal arm synchronizing assembly 955 ensures that the variable-length support assembly 950 extends and retracts in alignment with the central axis CA extending through the proximal coupler 405, the eyelets 475, and the distal coupler 415.

In the pictured embodiment, the proximal arm synchronizing assembly 955 comprises four gear elements 965a, 965b, 965c, and 965d. The gears 965a and 965c comprise one side of the proximal arm synchronizing assembly 955, and the gears 965b and 965d comprise the other side of the proximal arm synchronizing assembly 955. The gears 965a and 965c of the proximal arm synchronizing assembly 955 are coupled to the proximal arm 470a, and the gears 965b and 965d of the proximal arm synchronizing assembly 955 are coupled to the proximal arm 470b. In some embodiments, the gears 965a-d are integral features of the proximal arms 470a, 470b. It is understood that the upper gears 965a, 965b and the lower gears 965c, 965d turn in opposing directions to synchronize the motion of the proximal arms 470a, 470b and the support members 962, 964. The gears 965a-d operate to (1) synchronize the proximal arms 470a, 470b, (2) to equally actuate the first and second support members 962, 964 of the variable-length support assembly 950 relative to one another, and (3) to stabilize and steady the connection between the proximal coupler 405 and the variable-length support assembly 950. Rotation of the gears 965a-d acts to constrain the motion of the proximal arms 470a, 470b to move through equal and opposite angles.

The distal arm synchronizing assembly 960 is substantially similar in structure and function to the proximal arm synchronizing assembly 955 includes four gear elements 970a, 970b, 970c, and 970d. The gears 970a and 970c comprise one side of the distal arm synchronizing assembly 960, and the gears 970b and 970d comprise the other side of the distal arm synchronizing assembly 960. The gears 970a and 970c of the distal arm synchronizing assembly 960 are coupled to the distal arm 472a, and gears 970b and 970d of the distal arm synchronizing assembly 960 are coupled to the distal arm 472b. In some embodiments, the gears 970a-d are integral features of the distal arms 472a, 472b.

Although a single set of gears could provide constraint against motion in both opposite transverse directions, it is noted that multiple sets of gears could share the load, thus allowing the arm synchronizing assemblies to withstand higher side loads than a single set of gears.

FIGS. 26A-2B illustrate perspective views of an exemplary instrument guiding apparatus 1000 according to another embodiment of the present disclosure. Instrument guiding apparatus 1000 can include a variable-length support assembly 1010 and an arm synchronizing assembly which can comprise a proximal arm synchronizing assembly 1020 and a distal arm synchronizing assembly 1030. Instrument guiding apparatus 1000, variable-length support assembly 1010, proximal arm synchronizing assembly 1020, and distal arm synchronizing assembly can be substantially similar to imaging guiding apparatus 400, variable-length support assembly 410, proximal arm synchronizing assembly 955, and distal arm synchronizing assembly 960 respectively, except for the differences described herein. FIG. 26A displays the instrument guiding apparatus 1000 from a top perspective while FIG. 26B displays the instrument guiding apparatus 1000 from a bottom perspective.

Figure 26B:
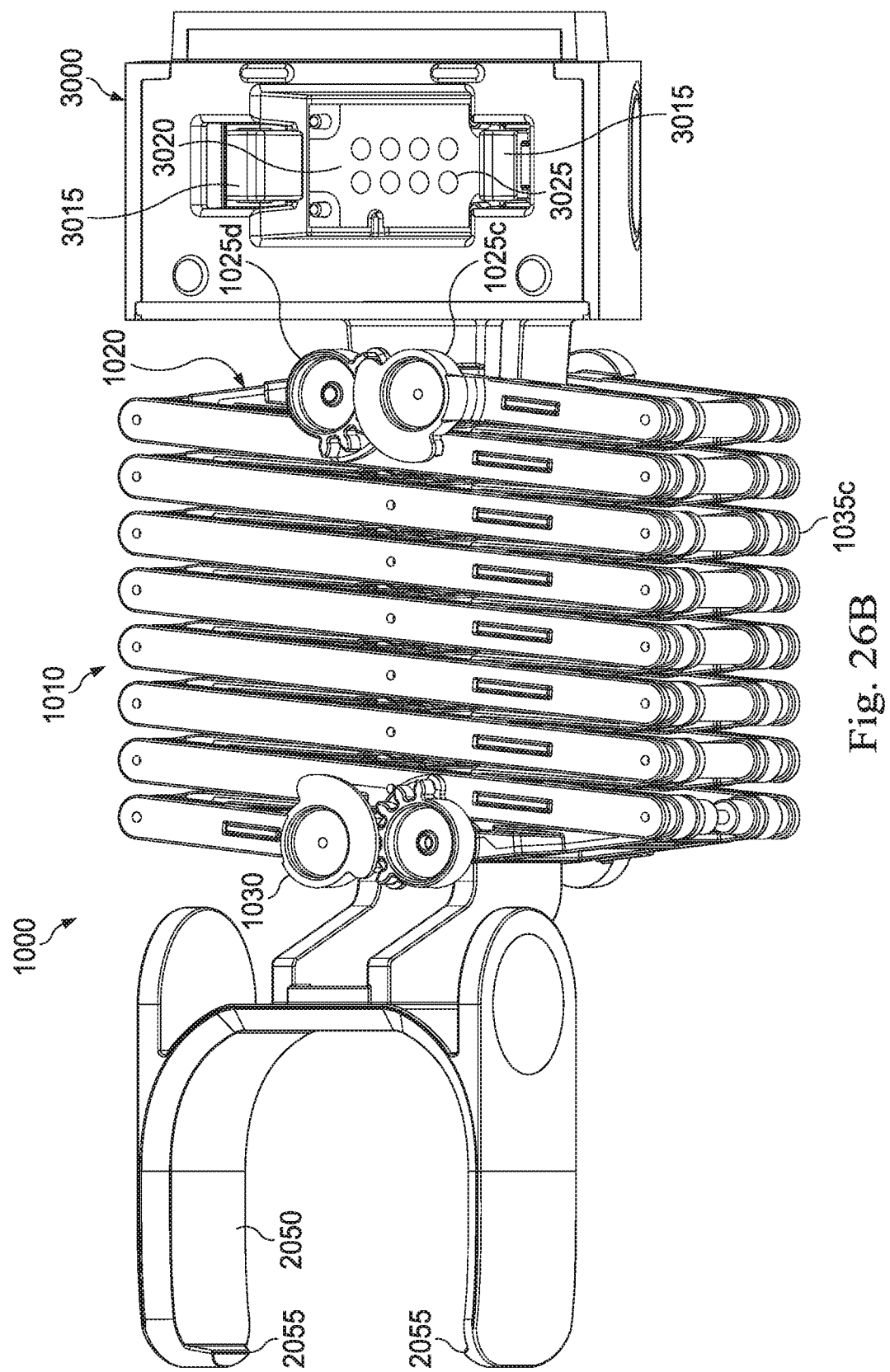

Proximal arm synchronizing assembly 1020 can comprise a first gear pair 1025a/1025b and a second gear pair 1025c/1025d positioned at the proximal end of the variable-length support assembly 1010. The gears 1025a-1025d can be substantially similar in structure and function to gears 965a-965d except for the differences described herein. In the illustrated embodiment, gears 1025a-1025d require less than 360 degree rotation to provide engagement of teeth during full extension and collapse of variable-length support assembly 1010. Thus gears 1025b and 1025d can be shaped as circular gear with a partial circumference of teeth as illustrated in FIGS. 26A, 26B, and 27A. Gears 1025a and 1025c can also include a partial circumference of teeth but as illustrated in FIGS. 26A, 26B, and 27A, gears 1025a and 1025c can each be shaped as a wedge instead of a circular gear. In an alternative embodiment illustrated in FIG. 27B, both gears may be shaped as wedges with a curved surface for a partial circumference of teeth. In yet another embodiment (not shown), both gears may be shaped as circular gears with a partial circumference of teeth.

In some embodiments, gears may provide potential pinch points for operators causing a safety concern. As illustrated in FIG. 27A, gear 1025a can include guard 1035a providing protection from a pinch-point between engaged teeth in gear pair 1025a/1025b. The single guard 1035a extending over the gear pair 1025a/1025b, allows for free rotational motion of the guard during expansion and compression of the variable-length support assembly 1010. In an alternative embodiment illustrated in FIG. 27B, gear 1025a' can be identical to gear 1025a but oriented in a mirrored image allowing guard 1035a' to rotate in a different plane than guard 1035a, avoiding interference between the guards. Gear pair 1025c/1025d may be substantially similar in structure and function as gear pair 1025a/2015b. Retelling back to FIGS. 26A and 26B, an enclosure 3000 may be provided which will be described in further detail below. In an alternative embodiment (not shown), the enclosure can be extended to cover gear pairs 1025a/1025b and 1025c/1025d, replacing guard 1035a and 1035c, and providing protection from potential pinch points.

The distal arm synchronizing assembly 1030 is substantially similar in structure and function to the proximal arm synchronizing assembly 1020. It should be understood that the distal synchronizing arm 1030 and the proximal arm synchronizing assembly 1020 can also include assemblies substantially similar to those described for synchronizing arm assemblies 600 including spools 605a and 605b and/or gears elements 965a, 965b, 965c, and 965d. The proximal arm synchronizing assembly 1020 and distal arm synchronizing assembly 1030 can use any combination of spools and gear assemblies, including any variation of gear embodiments described herein.

FIG. 28 illustrates a cross sectional view of the variable-length support assembly 1010 in a collapsed state with eyelets 1040 rotatably coupled to the support members 2010 using pins 2020. The eyelets 1040 are substantially similar to eyelet 475 and eyelet 905 disclosed above except for the differences described herein. In the pictured embodiment illustrated in FIG. 29A, the eyelet 1040 includes a body 1042 including a rectangular shaped distal surface 1045, a corresponding proximal surface 1055, and a lumen 1065 extending therebetween. The lumen 1065 may include chamfered edges where it terminates at the surfaces 1045, 1055 to permit easy passage of an instrument such as catheter 310, as described above for eyelet 705, eyelet 805, and eyelet

905. It should be understood that while eyelet 475, eyelet 505, and eyelet 605 are not illustrated with chamfered lumens, each eyelet can include chamfers for easy passage of the catheter 310. The body 1042 also includes an upper surface 1043a and a bottom surface 1043b.

As shown in FIGS. 29A and 29B, eyelet 1040 can also include alignment members 1075a-1075d. In this embodiment, alignment members 1075a-1075d are projections that extend laterally away from the body 1042. The edges of each alignment member 1075a-1075d can be curved away from the distal surface 1045 and away from the proximal surface 1045 toward a lateral tip 1076a-1076d, thus forming a tapered profile. In the embodiment of FIG. 29A, the tips 1076a-1076d are rounded and symmetric about a rotational axis R through the body 1042. In some embodiments, the ratio of the radius of curvature of the tip 1076a to the are length of the curved face of alignment member 1075a may be in a range of 0.0250-0.500. In one embodiment, for example, the radius of curvature of the tip 1076a may be 0.200 mm and the arc length of the curved face of alignment member 1075a may be approximately 5.100 mm. The tips 1076a-1076d may be continuously curved or may have a non-curved length bounded by surfaces with a radius of curvature. The outer edges of the alignment members 1075a-1075d may be curved away from the upper surface 1043a or the bottom surface 1043b toward the tips 1076a-1076d. When the variable-length assembly 1010 is in an expanded or un-collapsed configuration without an elongated flexible member extending through the eyelets 1040, the eyelets may be freely rotatable, for example, between 0° and 360°. The shape of the alignment members 1075a-1075d allows for self-alignment with adjacent eyelets 1040 as the support assembly 1010 is collapsed, resulting in the aligned stacking of adjacent eyelets 1040 such that the distal surface 1045 of one eyelet 1040 faces the proximal surface 1055 of an adjacent eyelet 1040. When the adjacent eyelet alignment members contact each other as the assembly is collapsed, the curved edges and tapered profile of the alignment members bias the series of eyelets 1040 toward alignment along a longitudinal axis through the lumen 1065. Once the alignment members 1075a-1075d of adjacent eyelets 1040 make contact with one another, the shape of the alignment members urge the eyelets 1040 into a stacked configuration such that the lumen 1065 of each of the eyelets 1040 are aligned. As viewed from a top perspective in FIG. 29B, the upper surface 1043a of eyelet 1040 can include a rectangular profile with the alignment members 1075a and 1075c extending away from the upper surface 1043a toward pointed oval ends.

FIGS. 30A and 30B illustrate an alternative embodiment of an eyelet 1050 with tapered alignment members 2005a-2005d. Alignment member 2005a curves from a distal surface 1085 towards a proximal surface 1095 to form a lateral tip 2006a while alignment member 2005c curves from the proximal surface 1095 towards the distal surface 1085 to form a lateral tip 2006c. A top view of eyelet 1050 is illustrated in FIG. 30B displaying the curved shape of the tapered alignment members 2005a-2005d including a curved parallelogram top profile with tips 2006a and 2006c. In some embodiments, the curved lateral surfaces of the parallelogram may be formed from a major curve, and the tip may be formed with a minor curve. The ratio of the radius of curvature of the minor curve to the major curve may be approximately 0.050-0.100. In one embodiment, for example, the minor curve forming the tip may have a radius of curvature of approximately 0.600 mm and the major curve forming the lateral curved surface of the parallelogram may be approximately 8.0 mm. In the embodiment of FIGS. 30A and 30B, the tips 2006a and 2006c are rounded, and the alignment member and tips are asymmetric about a rotational axis R through the eyelet 1050.

The shape of eyelets 1040 and 1050 can allow for more reliable self-alignment than other shapes. Non-curved alignment members could collapse into orthogonally misaligned positions relative to each other depending on an initial misalignment. For example, if a square or rectangular eyelet were misaligned by 90 degrees (i.e. rotated by 90 degrees about a longitudinal axis of a pin such as pin 2020), the misaligned eyelet would remain in the orthogonally misaligned configuration as the instrument guiding apparatus is collapsed. An oval shaped profile could help avoid a 90 degree misalignment but could still tend to lock in an orthogonally misaligned configuration. The shape of eyelet 1040 and eyelet 1050 include curved edges which converge to a curved point, the curved point helping to avoid locking in any initial misaligned configuration.

Referring back to FIGS. 26A and 26B, the enclosure 3000 can provide a housing for electronics such as printed circuit boards (PCBs) and sensors associated with the instrument guiding apparatus 1000, and/or mechanical fasteners including latches, mounting screws, magnetic connections, etc. for fixing the instrument guiding apparatus 1000 to an assembly such as teleoperational manipulator assembly 102 within teleoperated medical system 100. In one example, an instrument guiding apparatus PCB 3020 may be provided with electrical pads 3025 configured to mate with corresponding pogo pins on a system PCB (not shown) provided on the teleoperational manipulator assembly 102. A controller within the teleoperated medical system 100 can monitor and count a frequency of connecting and disconnecting the pogo pins with the system PCB in order to determine the number of times variable-length support assembly 1010 is mounted to the teleoperational manipulator assembly 102. In an alternative embodiment, the PCB can be replaced with a presence sensor indicating installation and/or removal of the instrument guiding apparatus 1000. In some embodiments, the presence sensor may be a life cycle indicator if the instrument guiding apparatus 1000 has a limited number of life cycles. The controller can save the number of connections of instrument guiding apparatus 1000 and provide an indication to the user when a new instrument guiding apparatus 1000 must be used for a next medical procedure. In one example, the support assembly PCB can include identification information and the controller can record a number of uses of the instrument guiding apparatus 1000 correlated to a specific identification part number representing the specific instrument guiding apparatus 1000. The enclosure 3000 may also include a coupling mechanism for detachably coupling an end of the instrument guiding apparatus 1000 to the teleoperational manipulator assembly 102 (not shown). In the illustrated embodiment of FIGS. 26A and 26B, the housing may include a pair of latches 3015 which can be actuated with buttons 3010 positioned on the outer surface of the enclosure 3000. The buttons may be depressed to compress the latches to mate with corresponding attachment elements (not shown) on the teleoperational manipulator assembly 102. In alternative embodiments the coupling mechanism may include any type of fastening element such as snap-fit engagements, frictional engagements, hook-and-eye fasteners, pins, magnetic fasteners, bolts (e.g. carriage bolts), screws (e.g. mating screws, thumb screws), and/or the like.

As illustrated in FIGS. 26A and 26B, a distal coupler 2050 may also be provided to detachably couple the distal end of the instrument guiding apparatus 1000 to a portion of the teleoperational manipulator assembly 102 such as a support arm included within the teleoperational manipulator assembly 102 (not shown). The distal coupler 2050 may include a C-shaped clamp constructed from a flexible material which can flex open with pressure to be installed onto the support arm and return to an original shape to lock onto the support arm. The support arm may include slots (not shown) which can mate with protrusions 2055 on the distal coupler 2050.

In alternative embodiments, the enclosure 3000 may be included on the distal end of the instrument guiding apparatus 1000 only or on both the distal and proximal ends of the instrument guiding apparatus 1000. Alternatively, a coupler such as illustrated in FIG. 26A may be included on the distal and/or proximal ends of instrument guiding apparatus 1000. Additionally, while the enclosure 3000 is illustrated in FIGS. 26A and 28B with respect to instrument guiding apparatus 1000, it should be understood that the enclosure 3000, electronics, mechanical fasteners, and controllers for counting of variable-length support assembly life cycles can be implemented within any embodiments of instrument guiding apparatus including but not limited to instrument guiding apparatus 400.

Assembly of an instrument guiding apparatus can require a complicated and time consuming assembly process. FIG. 31A illustrates an example of an assembly fixture 3500 for assembly of an instrument guiding apparatus 2500 which can facilitate an assembly process by providing a holding structure allowing for the instrument guiding apparatus 2500 to be assembled in separate sub-assembly layers. By providing separate sub-layers in a modular fashion, part count may be reduced, reducing cost and assembly time. FIG. 31A illustrates the instrument guiding apparatus 2500 fully assembled within the assembly fixture 3500. Instrument guiding apparatus 2500 can include a proximal coupler 2505, a distal coupler 2515, and a variable-length support assembly 2510, which comprises support members 2520, and eyelets 2530. As illustrated in FIG. 31B, each support member 2520 can include a lower support member 2525, an upper support member 2545, and an interior support member 2535. While assembly fixture 3500 is illustrated with instrument guiding apparatus 2500, it should be understood that assembly fixture 3500 can be used in a similar manner as described herein with instrument guiding apparatus 400, 960, and 1000 which are similar in structure and function to instrument guiding apparatus 2500.

FIG. 31B shows a single support member 2520 in an exploded configuration for illustration. During assembly of the instrument guiding apparatus 2500, a first subassembly layer can include the lower support members 2525 which can be loaded into slots 3510 within the assembly fixture 3500 which provides a stable support structure allowing for assembly of the instrument guiding apparatus 2500 in separate subassembly layers. A second subassembly layer including the eyelets 2530, interior support members 2535, pins 2550 for rotatably coupling the eyelets 2530 to the interior support members 2535 and the lower support members 2525, and pins 2540 for coupling lower support members 2525 to the interior support members 2535. The distal coupling 2515 and proximal coupling 2505 can then be fitted at the ends of the variable length support assembly 2500. A third subassembly layer can include the upper support members 2545 which can be snapped into the lower support members using mechanical snap retainers. The assembly process allows for an easy method of assembly without the use of adhesive, screws, and other fasteners requiring the use of tools.

The systems and methods of this disclosure are suited for use in the connected bronchial passageways of the lung, as well as for navigation and treatment of other tissues, via natural or surgically created connected passageways, in any of a variety of anatomical systems including the colon, the intestines, the kidneys, the brain, the heart, the circulatory system, the reproductive system, or the like. The methods and embodiments of this disclosure are also suitable for non-interventional applications.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An apparatus for guiding an elongated flexible instrument, the apparatus comprising:
 a variable-length support assembly including:
  a first end;
  a second end;
  a plurality of support member pairs, each support member pair comprising a first support member linked to a second support member; and
  a plurality of eyelets configured to receive the elongated flexible instrument, each of the plurality of eyelets movably coupled to at least one of the plurality of support member pairs along a longitudinal central axis between the first end and the second end,
 wherein the variable-length support assembly is configured to selectively transition from a compressed configuration to an expanded configuration along the longitudinal central axis, and wherein the plurality of eyelets are adapted to support the elongated flexible instrument as the elongated flexible instrument is advanced along the longitudinal central axis, and wherein each of the plurality of eyelets includes a tapered alignment member configured to contact a tapered alignment member of an adjacent eyelet to move the plurality of eyelets into alignment along the longitudinal central axis as the variable-length support assembly transitions from the expanded configuration to the compressed configuration.

2. The apparatus of claim 1, wherein each of the plurality of eyelets comprise a chamfered lumen for receiving the elongated flexible instrument.

3. The apparatus of claim 1 wherein the first support member includes an upper support portion, an interior support portion, and a lower support portion, wherein the upper support portion extends through the interior support portion to couple to the lower support portion.

4. The apparatus of claim 3 wherein the lower support portion extends through the interior support portion to couple to the upper support portion.

5. The apparatus of claim 1, wherein adjacent support member pairs are connected to each other by outer hinges.

6. The apparatus of claim 1, further comprising a proximal coupler at the first end of the variable-length support assembly, the proximal coupler configured to couple the variable-length support assembly to an instrument interface portion.

7. The apparatus of claim 6, wherein the proximal coupler includes a proximal aperture sized to receive the elongated flexible instrument, wherein the proximal aperture is aligned with the plurality of eyelets along the longitudinal central axis.

8. The apparatus of claim 6, further comprising a proximal arm synchronizing assembly coupled to the proximal coupler and the variable-length support assembly, the proximal arm synchronizing assembly configured to equally actuate the first and second support members relative to the longitudinal central axis and relative to each other.

9. The apparatus of claim 8, the proximal arm synchronizing assembly comprising a pair of spools and a set of cables wound in opposing S-shapes about the pair of spools.

10. The apparatus of claim 8, the proximal arm synchronizing assembly comprising a pair of gears.

11. The apparatus of claim 6, further comprising a retaining assembly coupled to the proximal coupler, the retaining assembly configured to selectively retain the variable-length support assembly in a compressed configuration.

12. The apparatus of claim 11, further comprising an attachment element at a distal end of the variable-length support assembly, wherein the retaining assembly selectively engages the attachment element to retain the variable-length support assembly in the compressed configuration.

13. The apparatus of claim 1, further comprising a distal coupler at the second end of the variable-length support assembly, the distal coupler configured to couple the variable-length support assembly to an anchor in a surgical field.

14. The apparatus of claim 1, wherein, for each eyelet of the plurality of eyelets, the first and second support members of the at least one of the plurality of support member pairs include indentations having a corresponding shape to the tapered alignment member, wherein the tapered alignment member is interposed between the indentations of the first and second support members when the variable-length support assembly assumes the compressed configuration.

15. The apparatus of claim 1, further comprising a torsion spring extending between each of the plurality of eyelets and respective first and second support members.

16. The apparatus of claim 1, further comprising a pair of magnets coupled to a set of adjacent eyelets and positioned between the adjacent eyelets.

17. The apparatus of claim 16, wherein the pair of magnets comprises a first magnet coupled to a first eyelet of the set of adjacent eyelets and a second magnet coupled to a second eyelet of the set of adjacent eyelets, the first magnet having an opposite polarity of the second magnet.

18. The apparatus of claim 1, further comprising a spring flexure extending between each of the plurality of eyelets and respective first and second support members.

19. The apparatus of claim 1 further comprising a sensor adapted to count each use of the variable-length support assembly.

20. The apparatus of claim 1, wherein each of the plurality of eyelets is freely rotatable about a rotation axis perpendicular to the longitudinal central axis when the variable-length support assembly is in the expanded configuration.

* * * * *